US008996131B1

(12) United States Patent
Owen et al.

(10) Patent No.: US 8,996,131 B1
(45) Date of Patent: *Mar. 31, 2015

(54) APPARATUS AND METHOD FOR MANAGING CHRONIC PAIN WITH INFRARED LIGHT SOURCES AND HEAT

(75) Inventors: James M. Owen, Redmond, WA (US); Matthew D. Keller, Kirkland, WA (US); Shuming Yuan, Bothell, WA (US)

(73) Assignee: Lockheed Martin Corporation, Bethesda, MD (US)

( * ) Notice: Subject to any disclaimer, the term of this patent is extended or adjusted under 35 U.S.C. 154(b) by 870 days.

This patent is subject to a terminal disclaimer.

(21) Appl. No.: 13/217,197

(22) Filed: Aug. 24, 2011

Related U.S. Application Data

(60) Provisional application No. 61/386,461, filed on Sep. 24, 2010, provisional application No. 61/511,020, filed on Jul. 22, 2011, provisional application No. 61/511,048, filed on Jul. 23, 2011, provisional application No. 61/511,050, filed on Jul. 23, 2011.

(51) Int. Cl.
*A61N 5/06* (2006.01)

(52) U.S. Cl.
USPC ................. 607/116; 607/88; 607/89; 607/92; 607/118

(58) Field of Classification Search
CPC .................................................... A61N 1/0556
USPC ................................ 607/88, 89, 92, 116, 118
See application file for complete search history.

(56) References Cited

U.S. PATENT DOCUMENTS 3,786,861 A     1/1974  Eggers
4,064,872 A    12/1977  Caplan
(Continued)

FOREIGN PATENT DOCUMENTS

WO      WO 0025112      5/2000

OTHER PUBLICATIONS

Allegre, et al., "Stimulation in the rat of a nerve fiber bundle by a short UV pulse from an excimer laser", "NeuroScience Letters", 1994, pp. 261-264, vol. 180.
(Continued)

*Primary Examiner* — William Thomson
*Assistant Examiner* — Jeffrey Lipitz
(74) *Attorney, Agent, or Firm* — Charles A. Lemaire; Jonathan M. Rixen; Lemaire Patent Law Firm, P.L.L.C.

(57) ABSTRACT

Method and apparatus for infrared-light nerve stimulation-plus-therapeutic-heat (INS-plus-TH) that includes providing a plurality of light sources; providing a plurality of thermally conductive extensions configured to transfer heat generated by the plurality of light sources away from the plurality of light sources; emitting a plurality of infrared-light nerve-stimulation signals toward neural tissue of an animal from the plurality of light sources, wherein the emitted infrared-light nerve-stimulation signals are configured to generate action potentials in the neural tissue, and wherein the emitting of the plurality of infrared-light nerve-stimulation signals includes generating heat; controlling the emitting of the plurality of infrared-light nerve-stimulation signals to generate action potentials in the neural tissue; and transferring the heat generated by the plurality of light sources during the emitting of the plurality of infrared-light nerve-stimulation signals away from the plurality of light sources and into surrounding tissue of the animal using the plurality of thermally conductive extensions.

20 Claims, 20 Drawing Sheets

(56) References Cited

U.S. PATENT DOCUMENTS

| | | |
|---|---|---|
| 4,215,694 A | 8/1980 | Isakov et al. |
| 4,232,678 A | 11/1980 | Skovajsa |
| 4,296,995 A | 10/1981 | Bickel |
| 4,558,703 A | 12/1985 | Mark |
| 4,566,935 A | 1/1986 | Hornbeck |
| 4,596,992 A | 6/1986 | Hornbeck |
| 4,671,285 A | 6/1987 | Walker |
| 4,681,791 A | 7/1987 | Shibahashi et al. |
| 4,724,835 A | 2/1988 | Liss et al. |
| 4,768,516 A | 9/1988 | Stoddart et al. |
| 4,813,418 A | 3/1989 | Harris |
| 4,840,485 A | 6/1989 | Gratton |
| 4,928,695 A | 5/1990 | Goldman et al. |
| 4,930,504 A | 6/1990 | Diamantopoulos et al. |
| 4,972,331 A | 11/1990 | Chance |
| 4,989,605 A | 2/1991 | Rossen |
| 5,062,428 A | 11/1991 | Chance |
| 5,088,493 A | 2/1992 | Giannini et al. |
| 5,122,974 A | 6/1992 | Chance |
| 5,139,025 A | 8/1992 | Lewis et al. |
| 5,150,704 A | 9/1992 | Tatebayashi et al. |
| 5,151,909 A | 9/1992 | Davenport et al. |
| 5,152,278 A | 10/1992 | Clayman |
| 5,187,672 A | 2/1993 | Chance et al. |
| 5,192,278 A | 3/1993 | Hayes et al. |
| 5,212,386 A | 5/1993 | Gratton et al. |
| 5,213,093 A | 5/1993 | Swindle |
| 5,213,105 A | 5/1993 | Gratton et al. |
| 5,257,202 A | 10/1993 | Feddersen et al. |
| 5,259,382 A | 11/1993 | Kronberg |
| 5,261,822 A | 11/1993 | Hall et al. |
| 5,323,010 A | 6/1994 | Gratton et al. |
| 5,327,902 A | 7/1994 | Lemmen |
| 5,353,799 A | 10/1994 | Chance |
| 5,386,827 A | 2/1995 | Chance et al. |
| 5,402,778 A | 4/1995 | Chance |
| 5,419,312 A | 5/1995 | Arenberg et al. |
| 5,430,175 A | 7/1995 | Hess et al. |
| 5,445,146 A | 8/1995 | Bellinger |
| 5,464,960 A | 11/1995 | Hall et al. |
| 5,480,482 A | 1/1996 | Novinson |
| 5,484,432 A | 1/1996 | Sand |
| 5,548,604 A | 8/1996 | Toepel |
| 5,553,614 A | 9/1996 | Chance |
| 5,564,417 A | 10/1996 | Chance |
| 5,608,519 A | 3/1997 | Gourley et al. |
| 5,664,574 A | 9/1997 | Chance |
| 5,704,899 A | 1/1998 | Milo |
| 5,754,578 A | 5/1998 | Jayaraman |
| 5,755,752 A | 5/1998 | Segal |
| 5,792,051 A | 8/1998 | Chance |
| 5,796,889 A | 8/1998 | Xu et al. |
| 5,799,030 A | 8/1998 | Brenner |
| 5,851,223 A | 12/1998 | Liss et al. |
| 5,899,865 A | 5/1999 | Chance |
| 5,913,884 A | 6/1999 | Trauner et al. |
| 6,033,431 A | 3/2000 | Segal |
| 6,048,359 A | 4/2000 | Biel |
| 6,055,110 A | 4/2000 | Kintz et al. |
| 6,066,127 A | 5/2000 | Abe |
| 6,074,411 A | 6/2000 | Lai et al. |
| 6,104,957 A | 8/2000 | Alo et al. |
| 6,110,195 A | 8/2000 | Xie et al. |
| 6,152,882 A | 11/2000 | Prutchi |
| 6,171,239 B1 | 1/2001 | Humphrey |
| 6,184,542 B1 | 2/2001 | Alphonse |
| 6,224,969 B1 | 5/2001 | Steenbergen et al. |
| 6,246,892 B1 | 6/2001 | Chance |
| 6,254,637 B1 | 7/2001 | Lee et al. |
| 6,257,759 B1 | 7/2001 | Witonsky et al. |
| 6,258,082 B1 | 7/2001 | Lin |
| 6,263,221 B1 | 7/2001 | Chance et al. |
| 6,267,779 B1 | 7/2001 | Gerdes |
| 6,272,367 B1 | 8/2001 | Chance |
| 6,284,078 B1 | 9/2001 | Witonsky et al. |
| 6,294,109 B1 | 9/2001 | Ratna et al. |
| 6,301,279 B1 | 10/2001 | Garbuzov et al. |
| 6,310,083 B1 | 10/2001 | Kao et al. |
| 6,312,451 B1 | 11/2001 | Streeter |
| 6,314,324 B1 | 11/2001 | Lattner et al. |
| 6,324,429 B1 | 11/2001 | Shire et al. |
| 6,330,388 B1 | 12/2001 | Bendett et al. |
| 6,339,606 B1 | 1/2002 | Alphonse |
| 6,353,226 B1 | 3/2002 | Khalil et al. |
| 6,358,272 B1 | 3/2002 | Wilden |
| 6,363,188 B1 | 3/2002 | Alphonse |
| 6,417,524 B1 | 7/2002 | Alphonse |
| 6,421,474 B2 | 7/2002 | Jewell et al. |
| 6,444,313 B1 | 9/2002 | Ono et al. |
| 6,456,866 B1 | 9/2002 | Tyler et al. |
| 6,459,715 B1 | 10/2002 | Khalfin et al. |
| 6,475,800 B1 | 11/2002 | Hazen et al. |
| 6,488,704 B1 | 12/2002 | Connelly et al. |
| 6,493,476 B2 | 12/2002 | Bendett |
| 6,505,075 B1 | 1/2003 | Weiner |
| 6,542,530 B1 | 4/2003 | Shieh et al. |
| 6,542,772 B1 | 4/2003 | Chance |
| 6,546,291 B2 | 4/2003 | Merfeld et al. |
| 6,556,611 B1 | 4/2003 | Khalfin et al. |
| 6,564,076 B1 | 5/2003 | Chance |
| 6,585,411 B2 | 7/2003 | Hammarth et al. |
| 6,592,611 B1 | 7/2003 | Zawada |
| 6,630,673 B2 | 10/2003 | Khalil et al. |
| 6,636,678 B1 | 10/2003 | Bendett et al. |
| 6,639,930 B2 | 10/2003 | Griffel et al. |
| 6,669,379 B2 | 12/2003 | Janosik et al. |
| 6,669,765 B2 | 12/2003 | Senga et al. |
| 6,688,783 B2 | 2/2004 | Janosik et al. |
| 6,690,873 B2 | 2/2004 | Bendett et al. |
| 6,735,474 B1 | 5/2004 | Loeb et al. |
| 6,735,475 B1 | 5/2004 | Whitehurst et al. |
| 6,744,548 B2 | 6/2004 | Abeles |
| 6,746,473 B2 | 6/2004 | Shanks et al. |
| 6,748,275 B2 | 6/2004 | Lattner et al. |
| 6,823,109 B2 | 11/2004 | Sasaki et al. |
| RE38,670 E | 12/2004 | Asah et al. |
| 6,836,685 B1 | 12/2004 | Fitz |
| 6,871,084 B1 | 3/2005 | Kingsley et al. |
| 6,902,528 B1 | 6/2005 | Garibaldi et al. |
| 6,909,826 B2 | 6/2005 | Cai et al. |
| 6,921,413 B2 | 7/2005 | Mahadevan-Jansen et al. |
| 6,953,341 B2 | 10/2005 | Black |
| 6,956,650 B2 | 10/2005 | Boas et al. |
| 6,980,579 B2 | 12/2005 | Jewell |
| 6,989,023 B2 | 1/2006 | Black |
| 7,003,353 B1 | 2/2006 | Parkhouse |
| 7,004,645 B2 | 2/2006 | Lemoff et al. |
| 7,006,749 B2 | 2/2006 | Illich et al. |
| 7,010,341 B2 | 3/2006 | Chance |
| 7,010,356 B2 | 3/2006 | Jog et al. |
| 7,031,363 B2 | 4/2006 | Biard et al. |
| 7,040,805 B1 | 5/2006 | Ou et al. |
| 7,068,878 B2 | 6/2006 | Crossman-Bosworth et al. |
| 7,069,083 B2 | 6/2006 | Finch et al. |
| 7,079,900 B2 | 7/2006 | Greenburg et al. |
| 7,085,300 B2 | 8/2006 | Werner et al. |
| 7,095,770 B2 | 8/2006 | Johnson |
| 7,116,886 B2 | 10/2006 | Colgan et al. |
| 7,124,810 B2 | 10/2006 | Lee et al. |
| 7,131,968 B2 | 11/2006 | Bendett et al. |
| 7,139,603 B2 | 11/2006 | Chance |
| 7,156,866 B1 | 1/2007 | Riggs et al. |
| 7,160,289 B2 | 1/2007 | Cohen |
| 7,177,081 B2 | 2/2007 | Tomita et al. |
| 7,190,993 B2 | 3/2007 | Sharma et al. |
| 7,194,063 B2 | 3/2007 | Dilmanian et al. |
| 7,225,028 B2 | 5/2007 | Della Santina et al. |
| 7,231,256 B2 | 6/2007 | Wahlstrand et al. |
| 7,244,253 B2 | 7/2007 | Neev |
| 7,302,296 B1 | 11/2007 | Hoffer |
| 7,311,722 B2 | 12/2007 | Larsen |
| 7,324,852 B2 | 1/2008 | Barolat et al. |
| 7,329,251 B2 | 2/2008 | Yamada et al. |
| 7,337,004 B2 | 2/2008 | Classen et al. |

(56) References Cited

U.S. PATENT DOCUMENTS

| | | | |
|---|---|---|---|
| 7,351,241 B2 | 4/2008 | Bendett et al. |
| 7,391,561 B2 | 6/2008 | Di Teodoro et al. |
| 7,402,167 B2 | 7/2008 | Nemenov |
| 7,488,341 B2 | 2/2009 | Merfeld |
| 7,647,112 B2 | 1/2010 | Tracey et al. |
| 7,654,750 B2 | 2/2010 | Brenner et al. |
| 7,736,382 B2 | 6/2010 | Webb et al. |
| 7,747,318 B2 | 6/2010 | John et al. |
| 7,756,588 B2 | 7/2010 | Jog et al. |
| 7,776,631 B2 | 8/2010 | Miles |
| 7,787,170 B2 | 8/2010 | Patel et al. |
| 7,792,588 B2 | 9/2010 | Harding |
| 7,797,029 B2 | 9/2010 | Gibson et al. |
| 7,801,601 B2 | 9/2010 | Maschino et al. |
| 7,803,454 B2 | 9/2010 | Toepel |
| 7,833,257 B2 | 11/2010 | Walsh, Jr. et al. |
| 7,873,085 B2 | 1/2011 | Babushkin et al. |
| 7,883,535 B2 | 2/2011 | Cantin et al. |
| 7,883,536 B1 | 2/2011 | Bendett et al. |
| 7,899,512 B2 | 3/2011 | Labadie et al. |
| 7,909,867 B2 | 3/2011 | Myung et al. |
| 7,914,842 B1 | 3/2011 | Greenberg et al. |
| 7,951,181 B2 | 5/2011 | Mahadevan-Jansen et al. |
| 7,988,688 B2 | 8/2011 | Webb et al. |
| 8,012,189 B1 | 9/2011 | Webb et al. |
| 2002/0002391 A1 | 1/2002 | Gerdes |
| 2003/0236458 A1 | 12/2003 | Hochman |
| 2004/0082984 A1* | 4/2004 | Osorio et al. | 607/105 |
| 2004/0225339 A1 | 11/2004 | Yaroslavsky et al. |
| 2005/0099824 A1 | 5/2005 | Dowling et al. |
| 2005/0143789 A1 | 6/2005 | Whitehurst et al. |
| 2006/0161218 A1 | 7/2006 | Danilov |
| 2006/0167564 A1 | 7/2006 | Flaherty et al. |
| 2006/0276861 A1 | 12/2006 | Lin |
| 2007/0053996 A1 | 3/2007 | Boyden et al. |
| 2007/0054319 A1 | 3/2007 | Boyden et al. |
| 2007/0191906 A1 | 8/2007 | Iyer et al. |
| 2007/0260297 A1 | 11/2007 | Chariff |
| 2007/0261127 A1 | 11/2007 | Boyden et al. |
| 2008/0009748 A1 | 1/2008 | Gratton et al. |
| 2008/0077200 A1 | 3/2008 | Bendett et al. |
| 2008/0086206 A1 | 4/2008 | Nasiatka et al. |
| 2008/0161697 A1 | 7/2008 | Chance |
| 2009/0030327 A1 | 1/2009 | Chance |
| 2009/0054954 A1 | 2/2009 | Foley |
| 2009/0076115 A1 | 3/2009 | Wharton et al. |
| 2009/0149926 A1* | 6/2009 | Dacey et al. | 607/96 |
| 2009/0163982 A1 | 6/2009 | deCharms |
| 2009/0177255 A1 | 7/2009 | Merfeld |
| 2009/0210039 A1 | 8/2009 | Boyden et al. |
| 2010/0049180 A1 | 2/2010 | Wells et al. |
| 2010/0114190 A1 | 5/2010 | Bendett et al. |
| 2010/0145418 A1 | 6/2010 | Zhang et al. |
| 2010/0162109 A1 | 6/2010 | Chatterjee et al. |
| 2010/0184818 A1 | 7/2010 | Wharton et al. |
| 2010/0292758 A1 | 11/2010 | Lee et al. |
| 2011/0172725 A1 | 7/2011 | Wells et al. |

OTHER PUBLICATIONS

Arridge, et al., "The theoretical basis for the determination of optical pathlengths in tissue: temporal and frequency analysis", "Phys. Med. Biol.", 1992, pp. 1531-1560, vol. 37.

Bernstein, Jacob G., et al., "Prosthetic systems for therapeutic optical activation and silencing of genetically-targeted neurons", "Proc Soc Photo Opt Instrum Eng.", May 5, 2008, vol. 6854: 68540H.

Boyden, Edward S., et al., "Millisecond-timescale, genetically targeted optical control of neural activity", "Nature Neuroscience", Sep. 2005, pp. 1263-1268, vol. 8, No. 9.

Chambers, James J., et al., "Light-Induced Depolarization of Neurons Using a Modified Shaker K+ Channel and a Molecular Photoswitch", "Journal of Neurophysiology", Jul. 26, 2006, pp. 2792-2796, vol. 96.

Dodt, H.-U., et al., "Precisely Localized LTD in the Neocortex Revealed by Infrared-Guided Laser Stimulation.", "Science", Oct. 1, 1999, pp. 110-113, vol. 286.

Han, Xue, et al., "Multiple-Color Optical Activation, Silencing, and Desynchronization of Neural Activity, with Single-Spike Temporal Resol", "PLoS ONE 2(3): e299. doi:10.1371/journal.pone. 0000299", Mar. 2007, p. e299, No. 3, Publisher: www.plosone.org.

Huang, Ying-Ying, et al., "Biphasic Dose Response in Low Level Light Therapy", "Dose-Response", 2009, pp. 358-383, vol. 7.

Izzo, et al., "Laser Stimulation of the Auditory Nerve", "Lasers in Surgery and Medicine", 2006, Publisher: Wiley-Liss, Inc.

Izzo, et al., "Selectivity of neural stimulation in the auditory system: a comparison of optic and electric stimuli", "Journal of Biomedical Optics", Mar./Apr. 2007, p. 021008, vol. 12, No. 2.

Nakagawa, Atsuhiro, et al., "Pulsed holmium:yttrium-aluminum-garnet laser-induced liquid jet as a novel dissection device in neuroendoscopic surgery", "J. Neurosurg.", Jul. 2004, pp. 145-150, vol. 101.

Passos, D., et al., "Tissue phantom for optical diagnostics based on a suspension of microspheres with a fractal size distribution", "Journal of Biomedical Optics.", Nov.-Dec. 2005, p. 064036, vol. 10, No. 6.

Princeton Lightwave (Company), "High Power Multimode Laser Arrays", "www.princetonlightwave.com/content/pli_high_power_multimode_laser_arrays.pd", 2005.

Princeton Lightwave (Company), "High Power Single Element Laser", "www.princetonlightwave.com/content/HP%20Single%20Element%20Laser%20version%202.pdf", 2005.

Rolfe, "In Vivo Near-Infrared Spectroscopy", "Annu. Rev. Biomed. Eng.", 2000, pp. 715-754, vol. 2.

Schiefer, et al., "A Model of Selective Activation of the Femoral Nerve with a Flat Interface Nerve Electrode for a Lower Extremity Neuopr", "IEEE Trans Neural Syst Rehabil Eng", Apr. 2008, pp. 195-204, vol. 16, No. 2.

Schwartz, et al., "Auditory Brainstem Implants", "Neurotherapeutics: The Journal of the American Soceity for Experimental Neuro Therapeutics", Jan. 2008, pp. 128-136, vol. 5.

Tarler, et al., "Comparison of joint torque evoked with monopolar and tripolar-cuff electrodes", "IEEE Trans Neural Syst Rehabil Eng", 2003, pp. 227-235, vol. 11, No. 3.

Teudt, et al., "Optical Stimulation of the Facial Nerve: A New Monitoring Technique?", "Laryngoscope", 2007, pp. 1641-1647, vol. 117, No. 9.

Vogel, Alfred, et al., "Mechanisms of pulsed laser ablation of biological tissues.", "Chemical Reviews", 2003, pp. 577-644, vol. 103, No. 2.

Wells, Jonathon, et al., "Application of Infrared Light for in vivo Neural Stimulation.", "Journal of Biomedical Optics", Nov. 2005, pp. 064003-1 to 064003-12, vol. 10, No. 6.

Wells, Jonathon, et al., "Optical stimulation of neural tissue in vivo", "Optics Letters", Mar. 1, 2005, pp. 504-506, vol. 30, No. 5.

Wells, Jonathon D., et al., "Optically Mediated Nerve Stimulation: Identification of Injury Thersholds.", "Lasers in Surgery and Medicine", Jul. 23, 2007, pp. 513-526, vol. 39.

Wells, Jonathon, et al., "Pulsed laser versus electrical energy for peripheral nerve stimulation", "Journal of Neuroscience Methods", 2007, pp. 326-337, vol. 163.

Zemelman, Boris V., et al., "Photochemical gating of heterologous ion channels: Remote control over genetically designated populations of neurons", "Proceedings of the National Academy of Sciences", Feb. 4, 2003, pp. 1352-1357, vol. 100, No. 3.

Allegre, et al., "Stimulation in the rat of a nerve fiber bundle by a short UV pulse from an excimer laser", "NeuroScience Letters", 1994, pp. 261-264, vol. 180.

Arridge, et al., "The theoretical basis for the determination of optical pathlengths in tissue: temporal and frequency analysis", "Phys. Med. Biol. ", 1992, pp. 1531-1560, vol. 37.

Augustine, George J., "Combining patch-clamp and optical methods in brain slices", "Journal of Neuroscience Methods", 1994, pp. 163-169, vol. 54.

Banghart, Matthew, et al., "Light-activated ion channels for remote control of neuronal firing", "Nature Neuroscience", Nov. 21, 2004, pp. 1381-1386, vol. 7, No. 12.

(56) References Cited

OTHER PUBLICATIONS

Bernstein, Jacob G., et al., "Prosthetic systems for therapeutic optical activation and silencing of genetically targeted neurons", "Proc Soc Photo Opt Instrum Eng.", May 5, 2008, vol. 6854: 68540H.

Boyden, Edward S., et al., "Millisecond-timescale, genetically targeted optical control of neural activity", "Nature Neuroscience ", Sep. 2005, pp. 1263-1268, vol. 8, No. 9.

Bureau, Ingrid, et al., "Precise Development of Functional and Anatomical Columns in the Neocortex", "Neuron", Jun. 10, 2004, pp. 789-801, vol. 42.

Chambers, James J., et al., "Light-Induced Depolarization of Neurons Using a Modified Shaker K+ Channel and a Molecular Photoswitch", "Journal of Neurophysiology", Jul 26, 2006, pp. 2792-2796, vol. 96.

Chance, et al., "Comparison of time-resolved and -unresolved measurements of deoxyhemoglobin in brain", "Proc. Nati. Acad. Sci. USA", Jul. 1988, pp. 4971-4975, vol. 85.

Deal, Walter J., et al., "Photoregulation of Biol. Activity by Photochromic Reagents, 3. Photoreg. Of Bioelectricity By Acetylcholine Receptor INH", "Proc. Natl. Acad. Sci.", 1969, pp. 1230-1234, vol. 64, No. 4.

Desmurget, et al., "Movement Intention after Parietal Cortex Stimulation in Humans", "Science", May 8, 2009, pp. 811-813, vol. 324.

Dodt, H.-U., et al., "Circuitry of rat barrel cortex investigated by infrared-guided laser stimulation", "NeuroReport", Mar. 24, 2003, pp. 623-627, vol. 14, No. 4.

Dodt, H.-U., et al., "Precisely Localized LTD in the Neocortex Revealed by Infrared-Guided Laser Stimulation.", "Science ", Oct 1, 1999, pp. 110-113, vol. 286.

Eder, Matthias, et al. , "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.

Fork, Richard L., "Laser Stimulation of Nerve Cells in Aplysia", "Science, New Series", Mar. 5, 1971, pp. 907-908, vol. 171, No. 3974.

Haggard, "The Sources of Human Volition", "Science", May 8, 2009, pp. 731-733, vol. 324.

Han, Xue, et al., "Multiple-Color Optical Activation, Silencing, and Desynchronization of Neural Activity, with Single-Spike Temporal Resol", "PLoS One 2(3): e299. doi:10.1371/journal.pone.0000299", Mar. 2007, pp. e299, No. 3, Publisher: www.plosone.org.

Huang, Ying-Ying, et al., "Biphasic Dose Response in Low Level Light Therapy", "Dose-Response", 2009, p. 358-383, vol. 7.

Izzo, et al., "Laser Stimulation of the Auditory Nerve", "Lasers in Surgery and Medicine", 2006, Publisher: Wiley Liss, Inc.

Izzo, et al., "Selectivity of neural stimulation in the auditory system: a comparison of optic and electric stimuli", "Journal of Biomedical Optics", Mar./Apr. 2007, pp. 021008 , vol. 12, No. 2.

Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, pp. 1108-1114, vol. 54, No. 6(1).

Maiorov, M., et al., "218 W quasi-CW operation of 1.83 um two-dimensional laser diode array", "Electronics Letters", Apr. 15, 1999, pp. 636-638, vol. 35, No. 8.

Nakagawa, Atsuhiro, et al., "Pulsed holmium:yttrium-aluminum-garnet laser-induced liquid jet as a novel dissection device in neuroendoscopic surgery", "J. Neurosurg. ", Jul. 2004 , pp. 145-150, vol. 101.

Naples, et al., "A spiral nerve cuff electrode for peripheral nerve stimulation", "IEEE Trans Biomed Eng", Nov. 1988, pp. 905-916, vol. 35, No. 11.

Passos, D., et al., "Tissue phantom for optical diagnostics based on a suspension of microspheres with a fractal size distribution", "Journal of Biomedical Optics.", Nov.-Dec. 2005 , pp. 064036, vol. 10, No. 6.

Princeton Lightwave (Company), "High Power Multimode Laser Arrays", "www.princetonlightwave.com/ content/pli_high_power_multimode_laser_arrays.pdf", 2005.

Princeton Lightwave (Company), "High Power Water Cooled Laser Stack", "www.princetonlightwave.com", 2005.

Wells, Jonathon, et al., "Pulsed laser versus electrical energy for peripheral nerve stimulation", "Journal of Neuroscience Methods ", 2007, pp. 326-337, vol. 163.

Yoo, et al., "Selective recording of the canine hypoglossal nerve using a multicontact flat interface nerve electrode", "IEEE Trans Biomed Eng", Aug. 2005, pp. 1461-1469, vol. 52, No. 8.

Zemelman, Boris V., et al., "Photochemical gating of heterologous ion channels: Remote control over genetically designated populations of neurons", "Proceedings of the National Academy of Sciences", Feb. 4, 2003, pp. 1352-1357, vol. 100, No. 3.

Zhang, Feng, et al. , "Channelrhodopsin-2 and optical control of excitable cells", "Nature Methods", Sep. 21, 2006, pp. 785-792, vol. 3, No. 10.

* cited by examiner

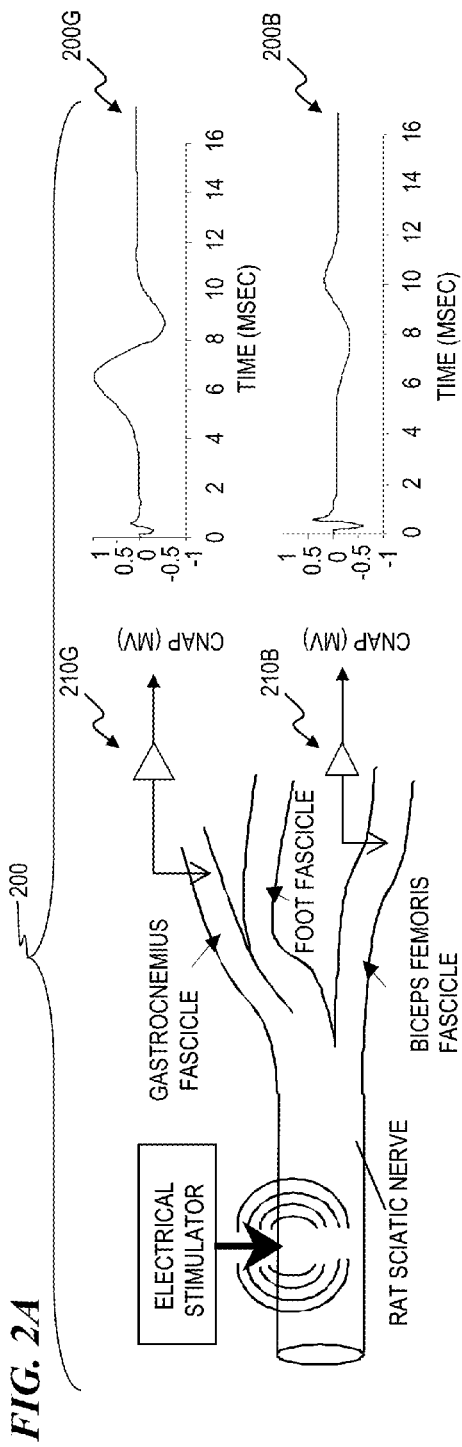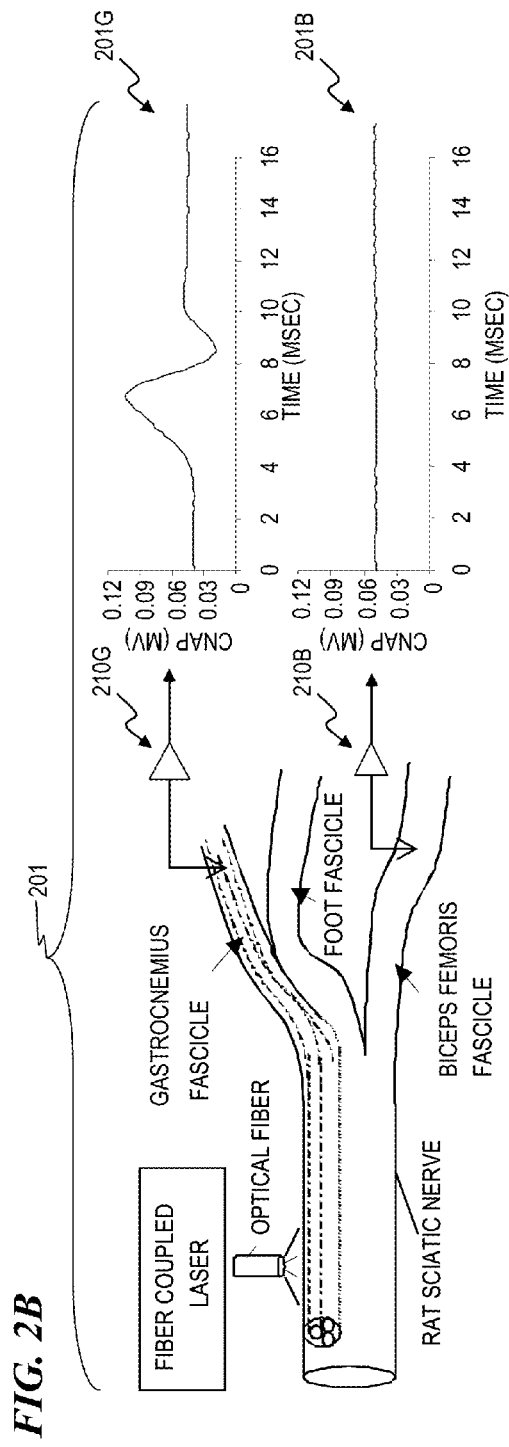

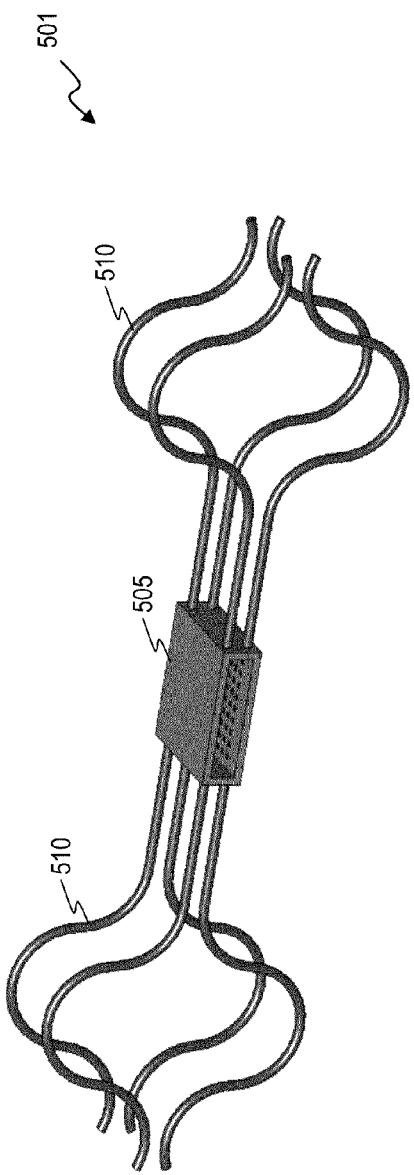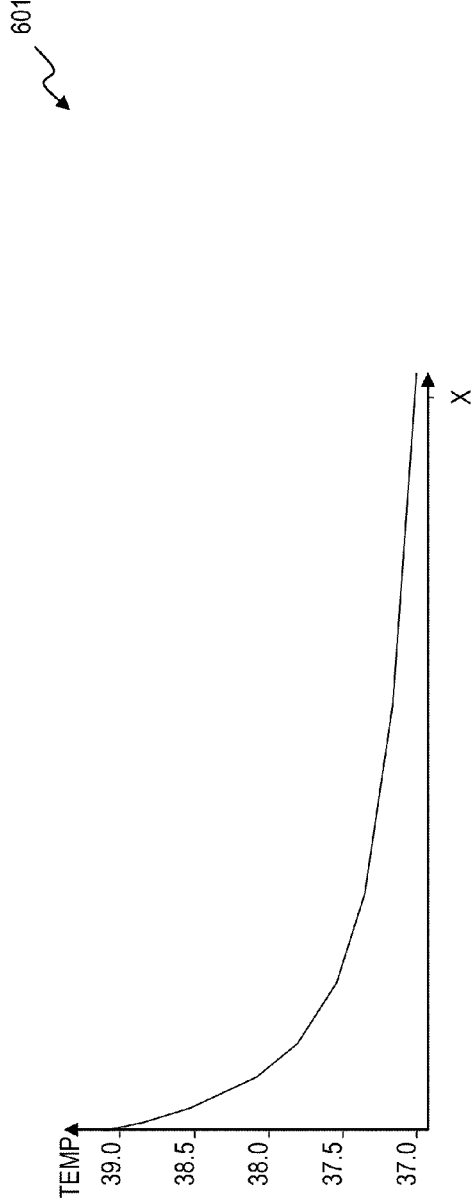
FIG. 5
FIG. 6

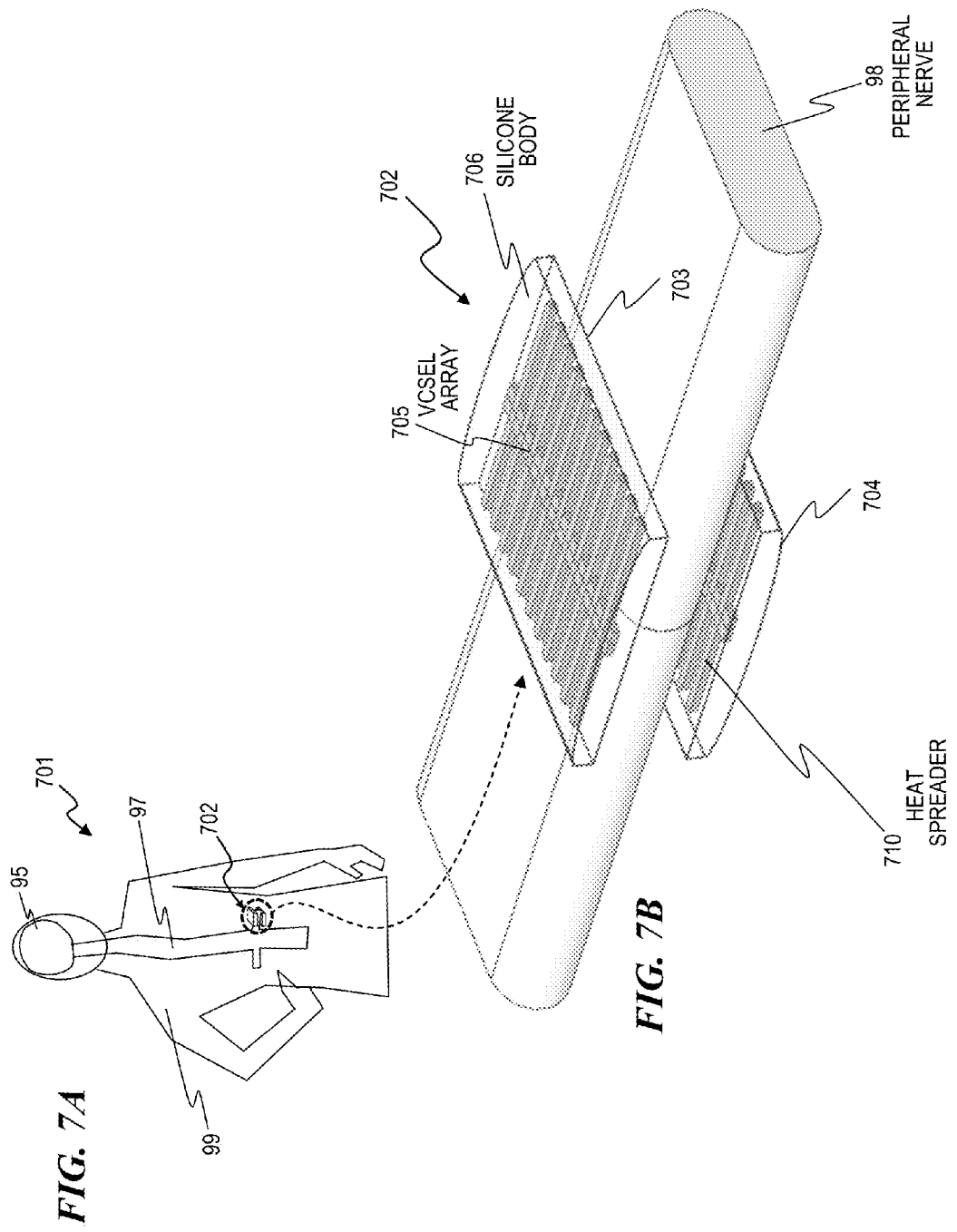

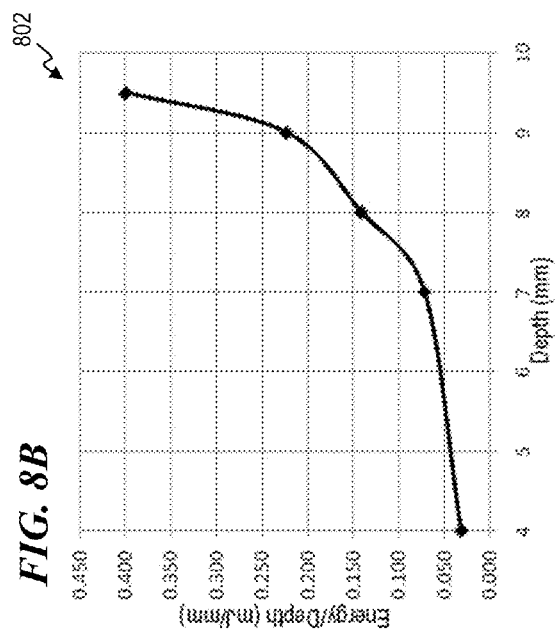
FIG. 8A
PULSE FORMAT REQUIRED FOR 0.4J/CM²
| IRRADIANCE | | 200 | 400 | 600 | 800 | 1100 |
|---|---|---|---|---|---|---|
| APERTURE SIZE | μm | 200 | 400 | 600 | 800 | 1100 |
| APERTURE AREA | cm^2 | 0.00031 | 0.00126 | 0.00283 | 0.00503 | 0.00950 |
| PULSE ENERGY | mJ/pulse | 0.126 | 0.503 | 1.131 | 2.011 | 3.801 |
| PEAK POWER | mW | 50 | 200 | 450 | 800 | 1512.5 |
| PULSE WIDTH | ms/pulse | 2.5 | 2.5 | 2.5 | 2.5 | 2.5 |
| 1/E DEPTH | mm | 4 | 7 | 8 | 9 | 9.5 |
| ENERGY/DEPTH | mJ/mm | 0.031 | 0.072 | 0.141 | 0.223 | 0.400 |
FIG. 8B
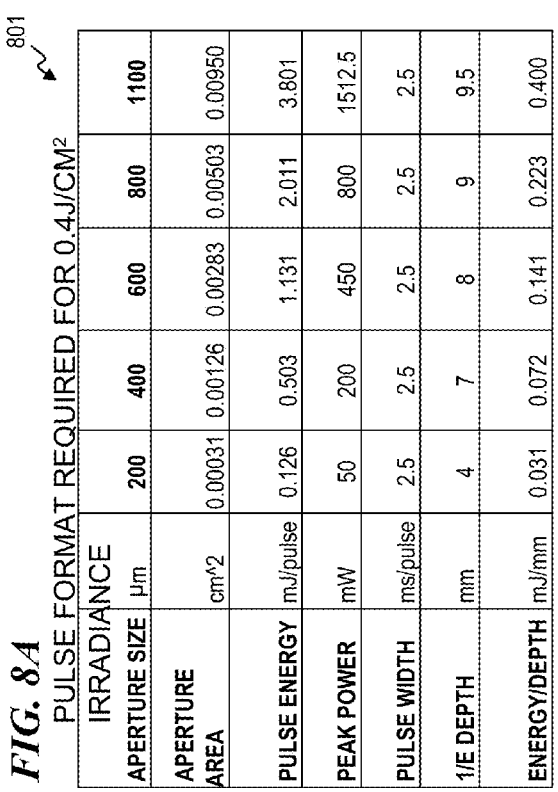
FIG. 8C
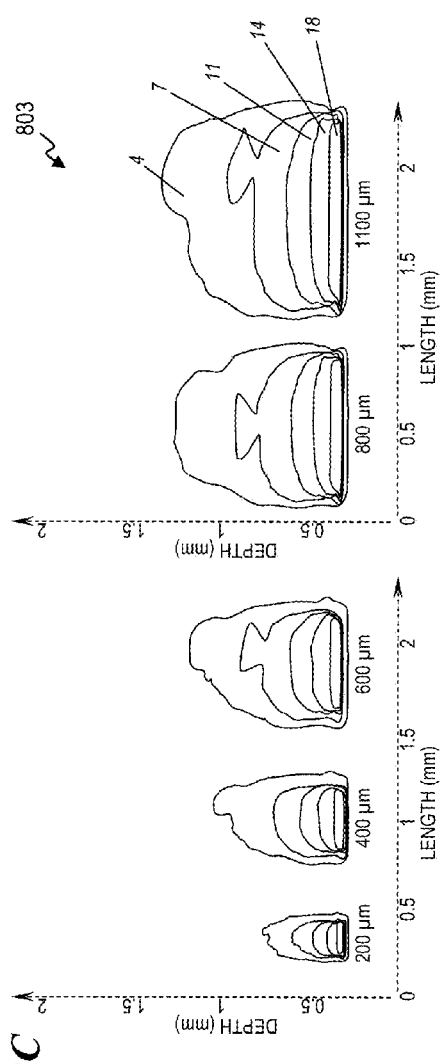

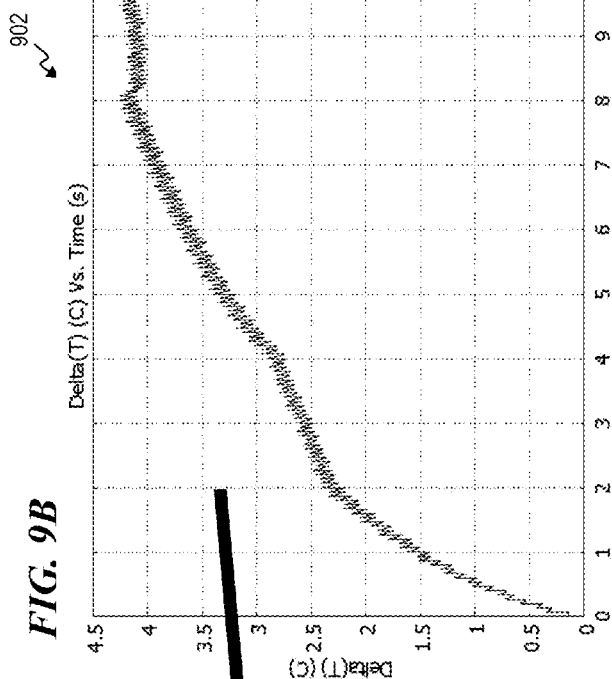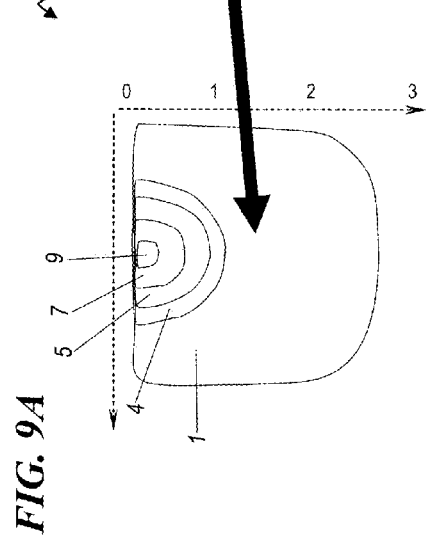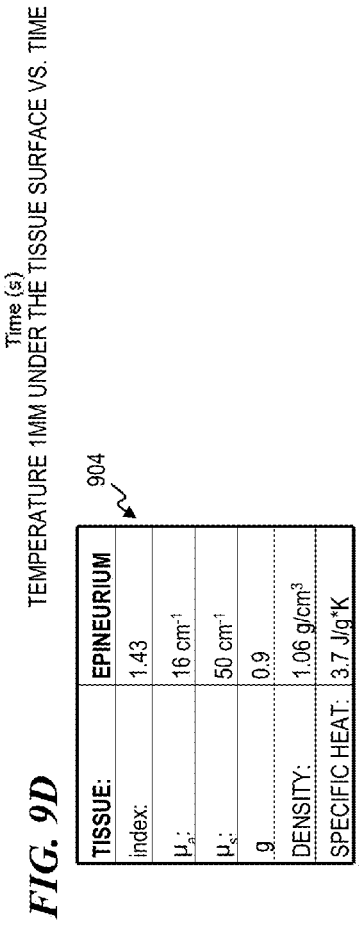
FIG. 9A
FIG. 9B
FIG. 9C
FIG. 9D

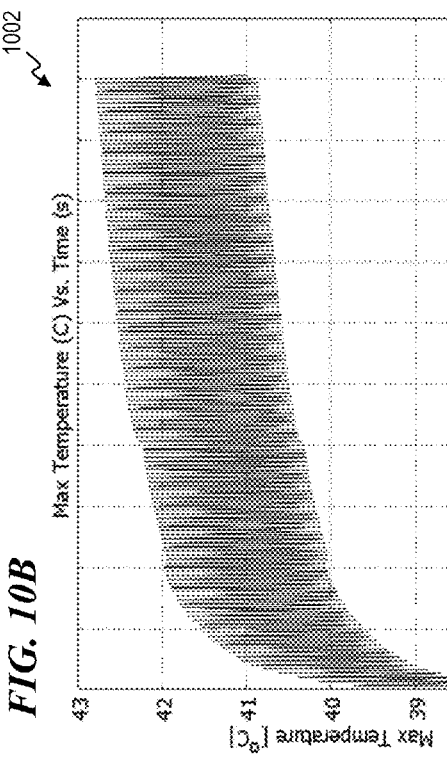
*FIG. 10A*
400-μm-APERTURE SIMULATION
*FIG. 10B*
MAXIMUM TEMPERATURE OF TISSUE SURFACE VS. TIME
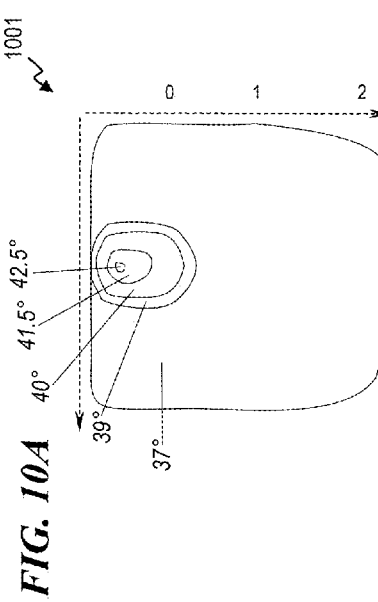
*FIG. 10C*
| APERTURE SIZE: | 400 μm |
| PULSE WIDTH: | 2.5 ms |
| PEAK POWER: | 260 mW |
| ENERGY/PULSE: | 0.65 mJ |
| PULSE RATE: | 15 Hz |
| RUN LENGTH: | 10 s |
| WAVELENGTH: | 1.87 μm |
| MAX TEMP.: | 42.5°C |
*FIG. 10D*
| TISSUE: | EPINEURIUM |
| index: | 1.43 |
| $\mu_a$: | 16 cm$^{-1}$ |
| $\mu_s$: | 50 cm$^{-1}$ |
| g | 0.9 |
| DENSITY: | 1.06 g/cm$^3$ |
| SPECIFIC HEAT: | 3.7 J/g*K |

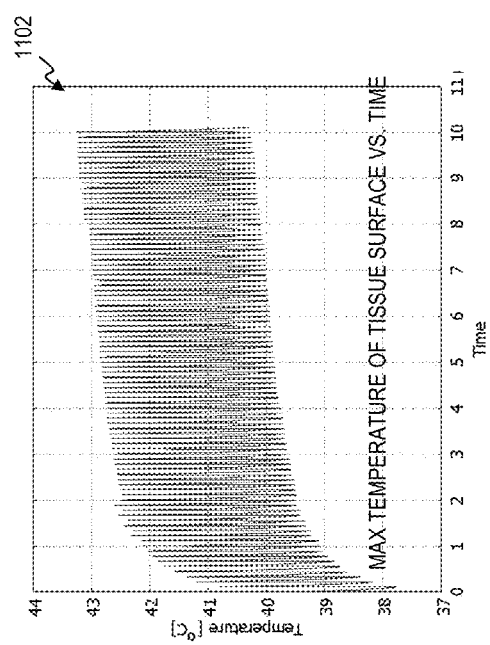
FIG. 11A
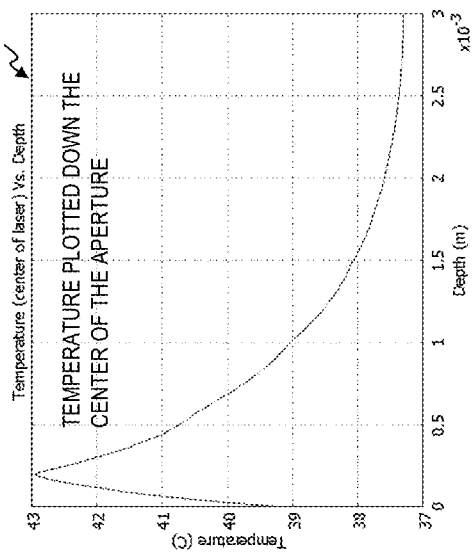
FIG. 11B
400-μm APERTURE SIMULATION
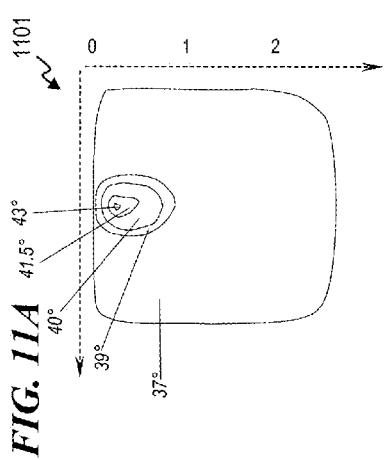
FIG. 11C
| APERTURE SIZE: | 400 μm |
| PULSE WIDTH: | 2.5 ms |
| PEAK POWER: | 400 mW |
| ENERGY/PULSE: | 1.04 mJ |
| PULSE RATE: | 9 Hz |
| RUN LENGTH: | 10 s |
| WAVELENGTH: | 1.87 μm |
| MAX TEMP: | 43°C |
FIG. 11D
| TISSUE: | EPINEURIUM |
|---|---|
| index: | 1.43 |
| $\mu_a$: | 16 cm$^{-1}$ |
| $\mu_s$: | 50 cm$^{-1}$ |
| g: | 0.9 |
| DENSITY: | 1.06 g/cm$^3$ |
| SPECIFIC HEAT: | 3.7 J/g*K |
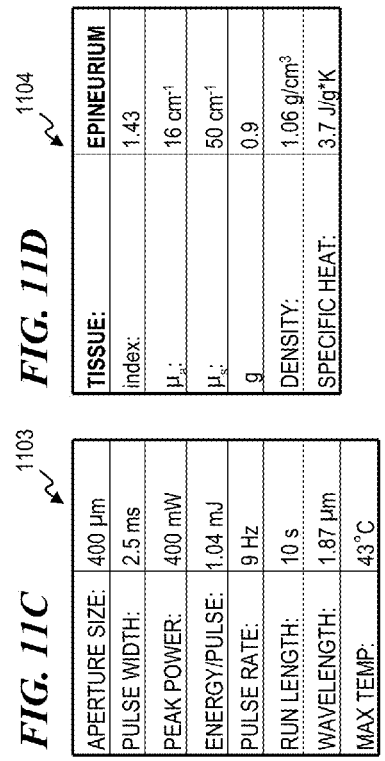
FIG. 11E

FIG. 12A THREE CHANNELS AT 1 MM SPACING

| APERTURE SIZE: | 400 µm |
| PULSE WIDTH: | 2.5 ms |
| PEAK POWER: | 200 mW |
| ENERGY/PULSE: | 0.5 mJ |
| PULSE RATE: | 15 Hz |
| RUN LENGTH: | 10 s |
| WAVELENGTH: | 1.87 µm |
| MAX TEMP: | 42.3°C |

| TISSUE: | EPINEURIUM |
| index: | 1.43 |
| $\mu_a$: | 16 cm$^{-1}$ |
| $\mu_s$: | 50 cm$^{-1}$ |
| g | 0.9 |
| DENSITY: | 1.06 g/cm$^3$ |
| SPECIFIC HEAT: | 3.7 J/g*K |

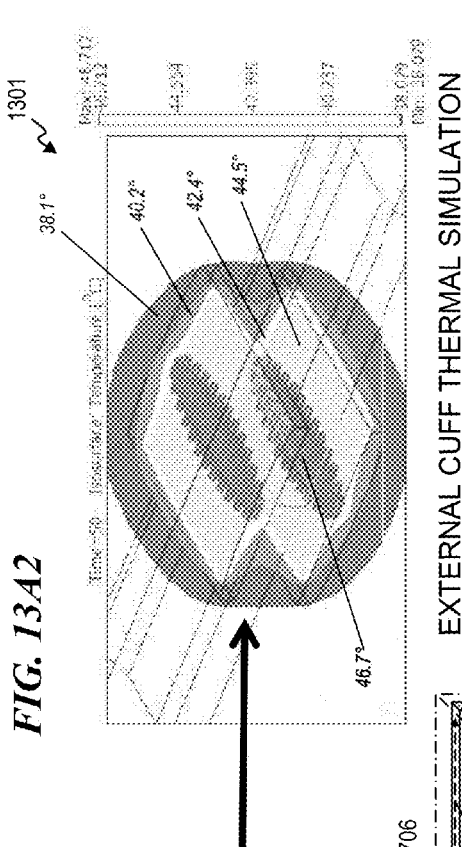
FIG. 13A1
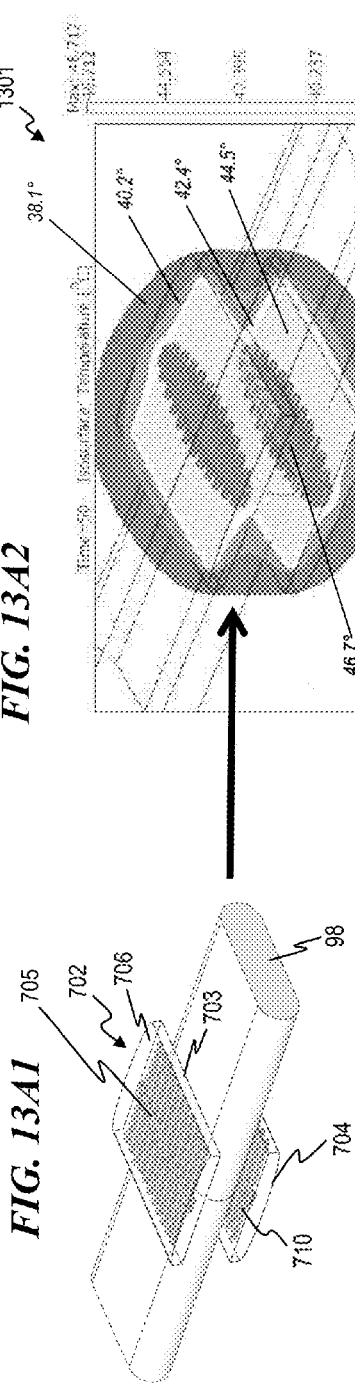
FIG. 13A2
EXTERNAL CUFF THERMAL SIMULATION
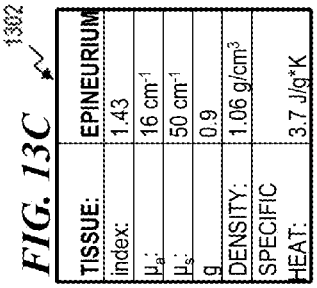
FIG. 13B
| APERTURE SIZE: | 400 μm |
|---|---|
| PULSE WIDTH: | 2.5 ms |
| PEAK POWER: | 200 mW |
| ENERGY/PULSE: | 0.5 mJ |
| PULSE RATE: | 15 Hz |
| RUN LENGTH: | 50 s |
| WAVELENGTH: | 1.87 μm |
| HEAT LOAD PER VCSEL: | 30 mW |
| VCSEL EFF.: | 25% |
| MAX TEMP.: | 46.7°C |
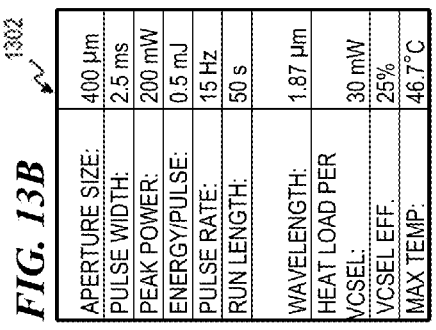
FIG. 13C
| TISSUE: | EPINEURIUM |
|---|---|
| index: | 1.43 |
| $\mu_a$: | 16 cm$^{-1}$ |
| $\mu_s$: | 50 cm$^{-1}$ |
| g | 0.9 |
| DENSITY: | 1.06 g/cm$^3$ |
| SPECIFIC HEAT: | 3.7 J/g*K |
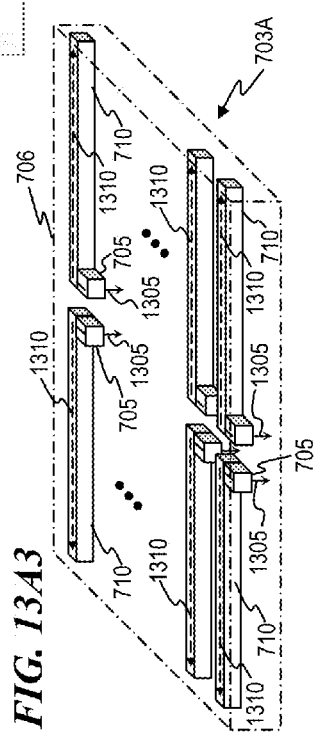
FIG. 13A3
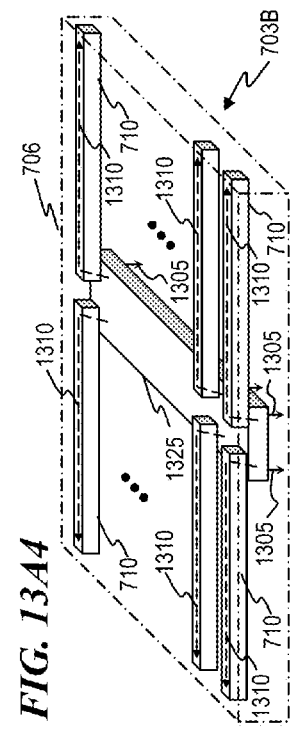
FIG. 13A4

1/8 OF THE MODEL TO BE SOLVED FOR SYMMETRY

CUFF TEMPERATURE, 15 HZ

TISSUE & CUFF, 15 HZ

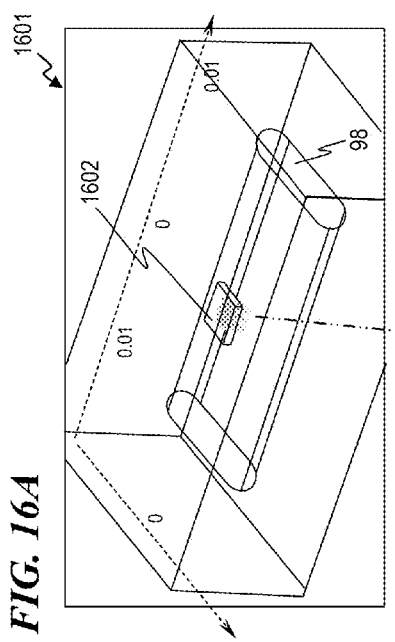
FIG. 16A
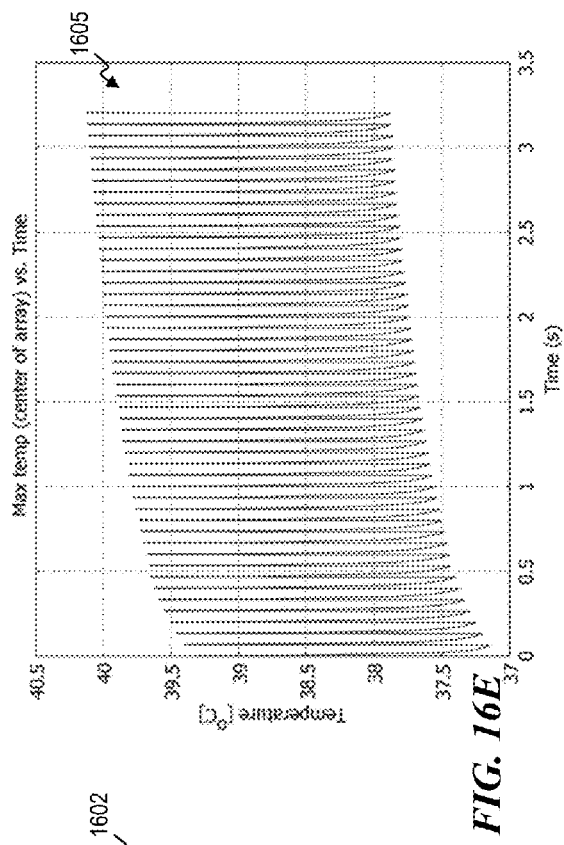
FIG. 16C
FIG. 16D
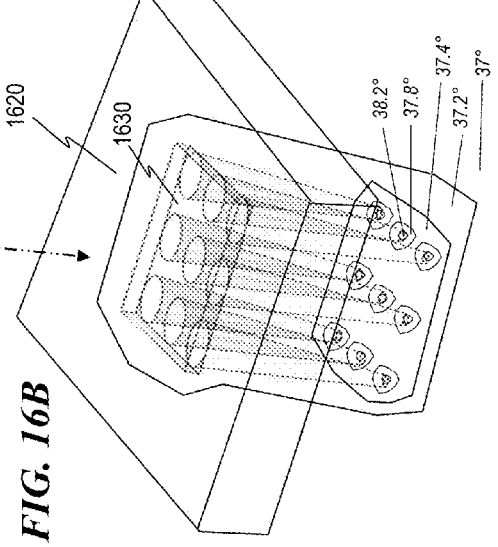
FIG. 16B
FIG. 16E

APPARATUS AND METHOD FOR MANAGING CHRONIC PAIN WITH INFRARED LIGHT SOURCES AND HEAT

CROSS-REFERENCE TO RELATED APPLICATIONS

This invention is related to:

U.S. Pat. No. 7,736,382 titled "APPARATUS FOR OPTICAL STIMULATION OF NERVES AND OTHER ANIMAL TISSUE" that issued Jun. 15, 2010 to James S. Webb et al., U.S. Pat. No. 7,883,536 titled "HYBRID OPTICAL-ELECTRICAL PROBES" that issued Feb. 8, 2011 to Mark P. Bendett et al., U.S. patent application Ser. No. 11/536,639 filed Sep. 28, 2006 by James S. Webb et al., titled "MINIATURE APPARATUS AND METHOD FOR OPTICAL STIMULATION OF NERVES AND OTHER ANIMAL TISSUE" (which issued as U.S. Pat. No. 7,988,688 on Aug. 2, 2011), U.S. patent application Ser. No. 11/948,912 filed Nov. 30, 2007 by James S. Webb et al., titled "APPARATUS AND METHOD FOR CHARACTERIZING OPTICAL SOURCES USED WITH HUMAN AND ANIMAL TISSUES", U.S. patent application Ser. No. 11/536,642 filed Sep. 28, 2006 by Mark P. Bendett et al., titled "APPARATUS AND METHOD FOR STIMULATION OF NERVES AND AUTOMATED CONTROL OF SURGICAL INSTRUMENTS" (which published as U.S. application publication 2008/007200 on Mar. 27, 2009), U.S. patent application Ser. No. 11/971,874 filed Jan. 9, 2008 by James S. Webb et al., titled "METHOD AND VESTIBULAR IMPLANT USING OPTICAL STIMULATION OF NERVES" (which issued as U.S. Pat. No. 8,012,189 on Sep. 6, 2011), U.S. patent application Ser. No. 12/191,301 filed Aug. 13, 2008 by Mark P. Bendett et al., titled "VCSEL ARRAY STIMULATOR APPARATUS AND METHOD FOR LIGHT STIMULATION OF BODILY TISSUES" (which issued as U.S. Pat. No. 8,475,506 on Jul. 2, 2013), U.S. patent application Ser. No. 12/254,832 filed Oct. 20, 2008 by Jonathon D. Wells et al., titled "SYSTEM AND METHOD FOR CONDITIONING ANIMAL TISSUE USING LASER LIGHT" (which published as U.S. Application Publication 2010/0049180 on Feb, 25, 2010), U.S. patent application Ser. No. 12/573,848 filed Oct. 5, 2009 by Mark P. Bendett et al., titled "NERVE STIMULATOR AND METHOD USING SIMULTANEOUS ELECTRICAL AND OPTICAL SIGNALS" (which issued as U.S. Pat. No. 8,160,696 on Apr. 17, 2012), U.S. patent application Ser. No. 13/013,816 filed Jan. 26, 2011 by Jonathon D. Wells et al., titled "NERVE STIMULATOR AND METHOD USING SIMULTANEOUS ELECTRICAL AND OPTICAL SIGNALS" (which issued as U.S. Pat. NO. 8,498,699 on Jul. 30, 2013), U.S. patent application Ser. No. 12/693,427 filed Jan. 25, 2010 by Daniel J. Lee et al., titled "OPTICAL STIMULATION OF THE BRAINSTEM AND/OR MIDBRAIN, INCLUDING AUDITORY AREAS" (which issured as U.S. Pat. No. 8,744,570 on Jun. 3, 2014), U.S. patent application Ser. No. 12/890,602 filed Sep. 24, 2010 by Jonathon D. Wells et al., titled "LASER-BASED NERVE STIMULATORS FOR, E.G., HEARING RESTORATION IN COCHLEAR PROSTHESES" (which issued as U.S. Pat. No. 8,792,978 on Jul. 29, 2014), U.S. patent application Ser. No. 13/117,121 filed May 26, 2011 by Jonathon D. Wells et al., titled "IMPLANTABLE INFRARED NERVE STIMULATION DEVICES FOR PERIPHERAL AND CRANIAL NERVE INTERFACES" (which published as U.S. Application Publication 2011/02953445 on Dec. 1, 2011), U.S. patent application Ser. No. 13/117,122 filed May 26, 2011 by Jonathon D. Wells et al., titled "CUFF APPARATUS AND METHOD FOR OPTICAL AND/OR ELECTRICAL NERVE STIMULATION OF PERIPHERAL NERVES" (which issued as U.S. Pat. No. 8,652,187 on Feb. 18, 2014), U.S. patent application Ser. No. 13/117,125 filed May 26, 2011 by Jonathon D. Wells et al., titled "NERVE-PENETRATING APPARATUS AND METHOD FOR OPTICAL AND/OR ELECTRICAL NERVE STIMULATION OF PERIPHERAL NERVES" (which published as U.S. Application Publication 2011/0295347 on Dec. 1, 2011), U.S. patent application Ser. No. 13/117,118 filed May 26, 2011 by Jonathon D. Wells et al., titled "OPTICAL BUNDLE APPARATUS AND METHOD FOR OPTICAL AND/OR ELECTRICAL NERVE STIMULATION OF PERIPHERAL NERVES" (which issued as U.S. Pat. No. 8,864,806 on Oct. 21, 2014), U.S. patent application Ser. No. 13/204,610 filed Aug. 5, 2011 by Michael E. Friend, titled "OCULAR IMPLANT AND METHOD FOR TRANSMISSION OF NERVE-STIMULATION LIGHT" (which issued as U.S. Pat. NO. 8,709,078 on Apr. 29, 2014), U.S. Provisional Patent Application 61/349,810 filed May 28, 2010 by Jonathon D. Wells et al., titled "Implantable Infrared Nerve Stimulation Devices for Peripheral and Cranial Nerve Interfaces", U.S. Provisional Patent Application 61/386,461 filed Sep. 24, 2010 by Jonathon D. Wells et al., titled "Implantable Infrared Nerve Stimulation Devices for Peripheral and Cranial Nerve Interfaces", U.S. Provisional Patent Application 61/511,020 filed Jul. 22, 2011 by Ryan C. Stafford, titled "METHOD AND APPARATUS FOR OPTIMIZING AN OPTICALLY STIMULATING COCHLEAR IMPLANT", U.S. Provisional Patent Application 61/511,048 filed Jul. 23, 2011 by Ryan C. Stafford, titled "BROAD WAVELENGTH PROFILE TO HOMOGENIZE THE ABSORPTION PROFILE IN OPTICAL STIMULATION OF NERVES", and U.S. Provisional Patent Application 61/511,050 filed Jul. 23, 2011 by Ryan C. Stafford et al., titled "OPTICAL COCHLEAR IMPLANT WITH ELECTRODE(S) AT THE APICAL END FOR STIMULATION OF APICAL SPIRAL GANGLION CELLS OF THE COCHLEA", each of which is incorporated herein by reference in its entirety. Benefit is claimed, under 35 U.S.C. 119(e)(1), of Provisional Patent Applications 61/386,461, 61/511,020, 61/511,048, and 61/511,050, listed above.

FIELD OF THE INVENTION

The invention relates generally to optical waveguides, and more particularly to apparatus and methods for obtaining and controlling optical signals from infrared (IR) sources (such as IR lasers and/or other nerve-stimulation-signal light sources), modulating the optical signals to form optical signals that are efficacious to control pain, and guiding the optical signals to the appropriate nerves using innovative waveguides, while conducting heat away from the controllers, lasers and/or other light sources and into surrounding tissue in order to use the heat as additional therapy.

BACKGROUND OF THE INVENTION

Chronic or recurrent pain affects 20-25% of the U.S. population, and it leads to approximately $100 billion in health care costs each year. The lost productivity due to pain is estimated at approximately $50 billion per year in the U.S. (low back pain is alone responsible for about a third of this figure). Traditional pain treatments include drugs (e.g., opioids (the world-wide market size for opioids (e.g., morphine and hydrocodone) is approximately $36 billion), anti-convulsants, anti-depressants, epidurals/anesthetics), surgery (e.g., disk surgery, nerve cutting), cognitive/behavioral (e.g., biopsychosocial approach, relaxation/biofeedback, placebo), and physical therapy. Other non-traditional approaches to pain management include acupuncture, ultrasound, and low-level light therapy (LLLT). The rule of thumb for leading pain researchers is that almost every major pain treatment creates about a 50% reduction in pain for 30-40% of patients (there is generally no good way to identify who will respond to a given treatment). Many drugs, particularly opioids, carry significant side effects and can become addictive. Depending on the study, 10-49% of back surgery patients are worse after the surgery ("failed back surgery syndrome").

For specific types of pain, or when more conservative approaches fail, electrical-signal stimulation (ES) is applied to neural tissue with "neuromodulation" devices to relieve the pain. These devices include peripheral nerve stimulators (PNS), deep brain stimulators (DBS), spinal cord stimulators (SCS), and transcutaneous electrical nerve stimulators (TENS). The first three types of devices are implanted, while TENS is applied on top of the skin. Combined, these devices include have the opportunity for an approximately $1.5 billion dollar market.

While these electrical-signal-stimulation devices can be effective, they often lack the specificity to target the specific neurons responsible for pain without also activating other sensory or motor neurons as a side effect (because electrical current spreads in the body, most if not all neuromodulation devices wind up stimulating other nerves in the area besides the intended target (e.g. causing tremors or unintended sensations)). The presence of a stimulation artifact can also obfuscate signals elsewhere along the nerve, which precludes stimulating and recording electrical nerve activity in the same or nearby locations.

U.S. Patent Application Publication 2005/0143789, filed Feb. 25, 2005 by Todd K. Whitehurst et al. (hereinafter, "Whitehurst et al."), titled "METHODS AND SYSTEMS FOR STIMULATING A PERIPHERAL NERVE TO TREAT CHRONIC PAIN", and is incorporated herein by reference. Whitehurst et al. describe treating chronic pain within a patient by applying at least one stimulus to a peripheral nerve within the patient with an implanted system control unit in accordance with one or more stimulation parameters. The stimulus is configured to treat the chronic pain.

U.S. Patent Application Publication 2006/0195146, filed Jan. 31, 2006 and published Aug. 31, 2006 (which issued as U.S. Pat. No. 7,647,112 on Jan. 12, 2010) by Michael R. Tracey et al. (hereinafter, "Tracey et al.") titled "SYSTEM AND METHOD FOR SELECTIVELY STIMULATING DIFFERENT BODY PARTS," and is incorporated herein by reference in its entirety. Tracey et al. describe electrically stimulating a predetermined body part of a mammal. The method includes placing at least one electrode in proximity to the mammal's skin, injecting an electrically conductive gel into the body of the mammal so as to form a conductive gel pathway extending at least partially along a distance between the at least one electrode and the predetermined body part, and stimulating the predetermined body part by applying an electrical signal via the electrode that travels, at least in part, through the conductive gel pathway.

U.S. Patent Application Publication 2006/0206163, filed Mar. 11, 2005 (which issued as U.S. Pat. No. 7,231,256 on Jun. 12, 2007) by Carl D. Wahlstrand et al. (hereinafter, "Wahlstrand et al."), titled "NEUROSTIMULATION SITE SCREENING", and is incorporated herein by reference. Wahlstrand et al. describe non-invasively screening a patient to select a stimulation site for treatment of head, neck or facial pain and tension symptoms caused by disorders such as occipital neuralgia. The screening process involves application of a transcutaneous stimulation screening device, a percutaneous micro-electrode screening device, and a temporary implantable screening device to the patient to select a site for chronic implantation.

U.S. Patent Application Publication 2007/0191906, filed Feb. 13, 2006 by Anand Iyer et al. (hereinafter, "Iyer et al."), titled "METHOD AND APPARATUS FOR SELECTIVE NERVE STIMULATION", and is incorporated herein by reference. Iyer et al. describe various device embodiments including at least a first and a second transducer, and a controller. The first transducer is adapted to be positioned to direct a first energy wave toward a neural target, and the second transducer is adapted to be positioned to direct a second energy wave toward the neural target. The controller is connected to the transducers to generate the first energy wave with a first predetermined phase and a first predetermined amplitude from the first transducer and to generate the second energy wave with a second predetermined phase and a second predetermined amplitude from the second transducer.

U.S. Patent Application Publication 2005/0216072, filed Mar. 3, 2005 (which issued as U.S. Pat. No. 7,951,181 on May 31, 2011) by Anita Mahadevan-Jansen et al. (hereinafter, "Mahadevan-Jansen et al."), titled "SYSTEM AND METHODS FOR OPTICAL STIMULATION OF NEURAL TISSUES", and is incorporated herein by reference. Mahadevan-Jansen et al. describe stimulating neural tissue of a living subject. The system includes an energy source capable of generating optical energy, a connector having a first end and a second end capable of transmitting optical energy, and a probe operably coupled to the second end of the connector and having an end portion for delivering optical energy to a target neural tissue.

U.S. Patent Application Publication 2007/0260297, filed Apr. 5, 2007 (which issued as U.S. Pat. No. 8,136,531 on Mar. 20, 2012) by Mark D. Chariff (hereinafter, "Chariff"), titled "DEVICE AND METHOD FOR TREATING MUSCULO-SKELETAL INJURY AND PAIN BY APPLICATION OF LASER LIGHT THERAPY", and is incorporated herein by reference. Chariff describes a laser therapy device and method of treatment for treating musculo-skeletal pain. The device and treatment employ a composite laser beam that includes multiple frequencies of laser energy.

U.S. Patent Application Publication 2009/0163982, filed Dec. 19, 2008 by Christopher R. deCharms (hereinafter, "deCharms"), titled "APPLICATIONS OF THE STIMULATION OF NEURAL TISSUE USING LIGHT", and is incorporated herein by reference. deCharms describes stimulating target tissue including a light source; an implantable light conducting lead coupled to said light source; and an implantable light-emitter. The light source, lead and emitter are used to provide a light stimulation to a target tissue.

U.S. Patent Application Publication 2009/0177255, filed Feb. 10, 2009 (which issued as U.S. Pat. No. 8,372,127 on Feb. 12, 2013) by Daniel M. Merfeld (hereinafter, "Merfeld"), titled "OPTICAL VESTIBULAR STIMULATOR", and is incorporated herein by reference. Merfeld describes an apparatus to stimulate the vestibular system of an individual. The apparatus includes an optical stimulator configured to optically stimulate a nerve area affecting a person's balance, and a control module coupled to the optical stimulator, the control module being configured to control the optical stimulator.

U.S. Patent Application Publication 2009/0076115, filed Feb. 28, 2006 (which issued as U.S. Pat. No. 8,207,211 on Jun. 26, 2012) by Tim Wharton et al. (hereinafter, "Wharton et al."), titled "PHOTOSENSITIZERS FOR TARGETED PHOTDYNAMIC THERAPY", and is incorporated herein by reference. Wharton et al. describe photosensitizer compounds based on functionalized fullerenes useful in targeted photodynamic therapy (PDT), and methods of use thereof.

U.S. Patent Application Publication 2010/0184818, filed Apr. 15, 2008 by John Timothy Wharton et al. (hereinafter, "Wharton et al."), titled "PHOTOSENSITIZERS FOR TARGETED PHOTDYNAMIC THERAPY", and is incorporated herein by reference. Wharton et al. describe photosensitizer compounds based on functionalized fullerenes useful in targeted photodynamic therapy (PDT), and methods of use thereof.

U.S. Pat. No. 4,813,418 to Frank W. Harris (hereinafter, "Harris"), titled "NERVE FIBER STIMULATION USING SYMMETRICAL BIPHASIC WAVEFORM APPLIED THROUGH PLURAL EQUALLY ACTIVE ELECTRODES", issued Mar. 21, 1989, and is incorporated herein by reference. Harris describes nerve fiber stimulation using a symmetrical biphasic waveform applied through plural active electrodes to increase the activity of the nerve fibers then selected for stimulation. Bi-phased pulse pairs are repeatedly symmetrically generated and applied to the nerve fibers to be stimulated with the first pulse of each pulse pair being a positive polarity pulse applied through a first electrode to cause the nerve fibers to be set into the refractory period and with the second pulse of each pulse pair being a negative polarity pulse applied through the first electrode to occur substantially at the end of the refractory period for the nerve fibers then to be stimulated to thereby excite those nerve fibers.

U.S. Pat. No. 5,851,223 to Saul Liss et al. (hereinafter, "Liss et al."), titled "COMBINATION NON-INTRUSIVE ANALGESIC NEUROAUGMENTIVE SYSTEM AND METHOD TRIPLE-MODULATED GIGATENS WITH OPTIONAL BIPOLAR SPIKE", issued Dec. 22, 1998, and is incorporated herein by reference. Liss et al. describe a system and apparatus for treating neurally responsive conditions by use of a novel combined waveform in combination with, and preferably modulated onto, a gigaTENS waveform administered to a patient.

U.S. Pat. No. 6,921,413 to Anita Mahadevan-Jansen et al. (hereinafter, "Mahadevan-Jansen et al."), titled "METHODS AND DEVICES FOR OPTICAL STIMULATION OF NEURAL TISSUES", issued Jul. 26, 2005, and is incorporated herein by reference. Mahadevan-Jansen et al. describe methods of directly stimulating neural tissue with optical energy. By stimulating neural tissue at wavelengths, laser pulses, and spot sizes disclosed herein, nerve stimulation be used to uniquely stimulate neural tissue in way not afforded by other means of stimulation.

U.S. Pat. No. 7,883,535 to Daniel Cantin et al. (hereinafter, "Cantin et al."), titled "DEVICE AND METHOD FOR TRANSMITTING MULTIPLE OPTICALLY-ENCODED STIMULATION SIGNALS TO MULTIPLE CELL LOCATIONS", issued Feb. 8, 2011, and is incorporated herein by reference. Cantin et al. describe transmitting multiple optically-encoded stimulation signals to multiple stimulation sites, especially cell locations. They use a primary optical fiber to transmit specific wavelength components of an encoded light signal to output positions along the fiber where they are coupled out of the primary fiber to stimulation sites via electrodes for electrical stimulation of the sites or optical windows and/or secondary optical fibers for photo-stimulation of sites.

U.S. Pat. No. 7,069,083 to Philip M. Finch et al. (hereinafter, "Finch et al.") titled "SYSTEM AND METHOD FOR ELECTRICAL STIMULATION OF THE INTERVERTEBRAL DISC", issued Jun. 27, 2006, and is incorporated herein by reference. Finch et al. describe electrically stimulating an area in a spinal disc. The method includes implanting a lead with one or more electrodes in a placement site in or adjacent to one or more discs at any spinal level from cervical through lumbar, connecting the lead to a signal generator, and generating electrical stimulation pulses using the generator to stimulate targeted portions of the disc.

U.S. Pat. No. 6,505,075 to Richard L. Weiner (hereinafter, "Weiner") titled "PERIPHERAL NERVE STIMULATION METHOD", issued Jan. 7, 2003, and is incorporated herein by reference. Weiner describes treating pain by subcutaneous electrical stimulation of a peripheral nerve. A lead is placed subcutaneously over a peripheral nerve that is causing pain. The peripheral nerve is electrically stimulated to cause paresthesia.

U.S. Pat. No. 7,324,852 to Giancarlo Barolat et al. (hereinafter, "Barolat et al.") titled "SYSTEM AND METHOD FOR NEUROLOGICAL STIMULATION OF PERIPHERAL NERVES TO TREAT LOW BACK PAIN", issued Jan. 29, 2008, and is incorporated herein by reference. Barolat et al. describe a system for neurological stimulation of peripheral nerve fibers to treat low back pain. The system includes stimulation electrodes adapted to be implanted in tissue proximate a network of peripheral nerve fibers located in and innervating a painful region of the low back area and to deliver electrical stimulation pulses to the network of peripheral nerve fibers located in and innervating the painful region of the low back area.

U.S. Pat. No. 6,836,685 to William R. Fitz (hereinafter, "Fitz") titled "NERVE STIMULATION METHOD AND APPARATUS FOR PAIN RELIEF", issued Dec. 28, 2004, and is incorporated herein by reference. Fitz describes stimulation of the central, peripheral, and autonomic with particular attention being given to the medial branch of the spinal nerve associated with a painful spinal facet joint so as to block pain impulses from reaching the spinal cord. The preferred apparatus includes a neurostimulator, and two or more electrodes which carry electrical pulses to the target nerves. The impulses are intense enough to cause stimulation of a given medial branch, and its articular branches, but not so large as to spread to the spinal cord itself. In the preferred embodiment the stimulator is physically small and battery operated facilitating implantation underneath the skin.

U.S. Pat. No. 6,104,957 to Kenneth M. Alo et al. (hereinafter, "Alo et al.") titled "EPIDURAL NERVE ROOT STIMULATION WITH LEAD PLACEMENT METHOD", issued Aug. 15, 2000, and is incorporated herein by reference. Alo et al. describe a method of managing chronic pain and/or symptoms of motor dysfunction produced by a variety of disorders or conditions. The method includes techniques for positioning one or more stimulation leads so as to enable delivery of electrical energy to epidural spinal nervous tissue, spinal ganglia, nerve plexi, or peripheral nerves using superior-to-inferior and/or trans-spinal advancement relative to a vertebral column and stimulating selected spinal nervous tissue.

U.S. Pat. No. 6,735,475 to Todd K. Whitehurst et al. (hereinafter, "Whitehurst et al.") titled "FULLY IMPLANTABLE MINIATURE NEUROSTIMULATOR FOR STIMULATION AS A THERAPY FOR HEADACHE AND/OR FACIAL PAIN", issued May 11, 2004, and is incorporated herein by reference. Whitehurst et al. describe a small implantable stimulator with at least two electrodes that is small enough to have the electrodes located adjacent to a nerve structure at least partially responsible for headache and/or facial pain. The small stimulator provides a means of stimulating a nerve structure(s) when desired, and may be implanted via a minimal surgical procedure.

U.S. Pat. No. 6,735,474 to Gerald E. Loeb et al. (hereinafter, "Loeb et al.") titled "IMPLANTABLE STIMULATOR SYSTEM AND METHOD FOR TREATMENT OF INCONTINENCE AND PAIN", issued May 11, 2004, and is incorporated herein by reference. Loeb et al. describe treatment of incontinence and/or pelvic pain that includes the injection or laparoscopic implantation of one or more battery- or radio-frequency-powered microstimulators beneath the skin of the perineum and/or adjacent the tibial nerve. The devices are programmed using radio-frequency control via an external controller that can be used by a physician to produce patterns of output stimulation pulses judged to be efficacious by appropriate clinical testing to diminish symptoms. The stimulation program is retained in the microstimulator device or external controller and is transmitted when commanded to start and stop by a signal from the patient or caregiver.

U.S. Pat. No. 4,989,605 to Joel Rossen (hereinafter, "Rossen") titled "TRANSCUTANEOUS ELECTRICAL NERVE STIMULATION (TENS) DEVICE", issued Feb. 5, 1991, and is incorporated herein by reference. Rossen describes an improved transcutaneous electrical nerve stimulator (TENS) involving a microcurrent (typically 25 to 900 microamps) monophase D.C. carrier signal (typically 10,000 to 19,000 Hz, preferably 15,000 Hz) that is modulated on and off in time (typically at 0.3 Hz up to 10,000 Hz, preferably 9.125 Hz followed by 292 Hz) and further inverted about every second by reversing the polarity of the signal at the electrodes.

U.S. Pat. No. 7,337,004 to Ashley M. Classen et al. (hereinafter, "Classen et al.") titled "METHOD AND APPARATUS FOR VETERINARY RF PAIN MANAGEMENT", issued Feb. 26, 2008, and is incorporated herein by reference. Classen et al. describe reducing chronic pain in animals by radio frequency (RF) neuromodulation of peripheral nerves of the animal. The method includes attaching active and dispersive percutaneous probes at respective active and dispersive locations relative to a peripheral nerve of the patient associated with the pain to be reduced; generating a first pulsed RF signal for coupling to the active and dispersive probes to verify the location of the peripheral nerve; and generating a second pulsed RF signal for coupling to the active and dispersive probes to modify propagation of pain sensation in the peripheral nerve without ablation thereof.

U.S. Pat. No. 6,074,411 to Ming Lai et al. (hereinafter, "Lai et al.") titled "MULTIPLE DIODE LASER APPARATUS AND METHOD FOR LASER ACUPUNCTURE THERAPY", issued Jun. 13, 2000, and is incorporated herein by reference. Lai et al. describe a laser apparatus and method for laser acupuncture therapy. A plurality of diode-laser modules, a self-adhesive holder for each of the modules, and a timer-controlled power supply are implemented.

U.S. Pat. No. 7,156,866 to Jeffrey M. Riggs et al. (hereinafter, "Riggs et al.") titled "HOLISTIC METHOD OF TREATING INJURED OR PATHOLOGIC TISSUE WITH A LASER", issued Jan. 2, 2007, and is incorporated herein by reference. Riggs et al. describe a holistic method of therapeutic laser treatment for body tissues in a problematic area, including the following steps: using a laser discharge probe to irradiate the tissues in the problematic area and additionally treating a body energy path through the problematic area by irradiating the body tissues along an energy path, as defined in Eastern medicine, through the problematic area so that energy flow is normalized in the problematic area.

U.S. Pat. No. 7,311,722 to Eric Larsen (hereinafter, "Larsen") titled "PHOTODYNAMIC STIMULATION DEVICE AND METHODS", issued Dec. 25, 2007, and is incorporated herein by reference. Larsen describes a treatment device that uses a light radiation of multiple wavelengths and pulse-shaped electromagnetic fields for the photodynamic stimulation of cells, especially cells of human tissue, and also for the activation and stimulation of light sensitive substances (PTD). The device produces energy radiation by the use of semiconductor and/or laser diodes, which emit light in several separate wavelengths due to a special operation mode and the use of tunable diodes.

U.S. Pat. No. 5,755,752 to Kim Robin Segal (hereinafter, "Segal") titled "DIODE LASER IRRADIATION SYSTEM FOR BIOLOGICAL TISSUE STIMULATION", issued May 26, 1998, and is incorporated herein by reference. Segal describes a diode-laser irradiation system for treating biological tissue of a subject without exposing the tissue to damaging thermal effects. The system includes a manipulable wand for contact with the tissue, a diode laser disposed in the wand for irradiating the tissue with coherent optical energy at a power output level of less than one thousand milliwatts, and laser setting controls for operating the diode laser to achieve a rate of absorption and conversion to heat in the irradiated tissue in a range between a minimum rate sufficient to elevate the average temperature of the irradiated tissue to a level above the basal body temperature of the subject, and a maximum rate which is less than the rate at which the irradiated tissue is converted into a collagenous substance.

U.S. Pat. No. 6,267,779 to Harold M. Gerdes (hereinafter, "Gerdes") titled "METHOD AND APPARATUS FOR THERAPEUTIC LASER TREATMENT", issued Jul. 31, 2001, and is incorporated herein by reference. Gerdes describes a therapeutic laser apparatus that includes at least two wands connected to a controller and radiation source via fiber optic cables. The controller and source include at least two infrared wavelength solid-state diode ("SSD") lasers and at least two visible wavelength SSD aiming lasers.

U.S. Pat. No. 4,671,285 to Walker (hereinafter, "Walker") titled "TREATMENT OF HUMAN NEUROLOGICAL PROBLEMS BY LASER PHOTO SIMULATION", issued Jun. 9, 1987, and is incorporated herein by reference. Walker describes a method of treating nerve damages in humans, and more particularly, to a noninvasive, nontraumatic method which includes the steps of applying an essentially monochromatic light to the skin area adjacent to the damaged nerve region of the body.

U.S. Pat. No. 5,445,146 to Gary J. Bellinger (hereinafter, "Bellinger") titled "BIOLOGICAL TISSUE STIMULATION BY LOW LEVEL OPTICAL ENERGY", issued Jul.

1, 1991, and is incorporated herein by reference. Bellinger describes biological tissue of a living subject is irradiated with optical energy at a wavelength and at a power dissipation level to cause the amount of optical energy absorbed and converted to heat in the tissue to be within a range bounded by a minimum absorption rate sufficient to elevate the average temperature of the irradiated tissue to a level above the basal body temperature, but which is less than the absorption rate at which tissue is converted into a collagenous substance. According to this method, a therapeutic, warming effect is produced within the irradiated tissue, but without causing tissue damage by thermal overheating. The method of using a low level reactive laser system from 100 milliwatts to 800 milliwatts in either a pulsed or continuous mode with optical energy produced by a Nd:YAG laser at a fundamental wavelength of 1064 nanometers has been found to reduce pain in soft tissues, reduce inflammation and enhance the healing of tissue by stimulation of microcirculation without subjecting the living tissue to damaging thermal effects. The energy density of the irradiated tissue is limited to the range of from about 1 joule per square centimeter to about 15 joules per square centimeter.

U.S. Pat. No. 6,033,431 to Kim Robin Segal (hereinafter, "Segal") titled "DIODE LASER IRRADIATION SYSTEM FOR BIOLOGICAL TISSUE STIMULATION", issued Mar. 7, 2000, and is incorporated herein by reference. Segal describes a diode laser irradiation system for treating biological tissue of a subject without exposing the tissue to damaging thermal effects. The system includes a manipulable wand for contact with the tissue, a diode laser disposed in the wand for irradiating the tissue with coherent optical energy at a power output level of less than one thousand milliwatts, and laser setting controls for operating the diode laser to achieve a rate of absorption and conversion to heat in the irradiated tissue in a range between a minimum rate sufficient to elevate the average temperature of the irradiated tissue to a level above the basal body temperature of the subject, and a maximum rate which is less than the rate at which the irradiated tissue is converted into a collagenous.

U.S. Pat. No. 4,232,678 to Joseph Skovajsa (hereinafter, "Skovajsa") titled "DEVICE FOR THE LOCAL TREATMENT OF A PATIENT, AND MORE PARTICULARLY APPLICABLE IN ACUPUNCTURE AND AURICULOTHERAPHY", issued Nov. 11, 1980, and is incorporated herein by reference. Skovajsa describes a device for the local treatment of a patient by acupuncture or auriculotherapy. Instead of needles, a treatment head is approached the body of the patient. It includes an infra-red laser diode being excitable recurrently and in a controlled manner. The recurrence frequency is selectable among a plurality of discrete frequencies, each of which may be finely adjusted.

U.S. Pat. No. 7,402,167 to Mikhail Nemenov (hereinafter, "Nemenov") titled "PORTABLE LASER AND PROCESS FOR PRODUCING CONTROLLED PAIN", issued Jul. 22, 2008, and is incorporated herein by reference. Nemenov describes a process and laser system for in vitro and in vivo pain research, pain clinical testing and pain management. In preferred embodiments of the invention a diode laser operating at a 980 nm wavelength is used to produce warmth, tickling, itching, touch, burning, hot pain or pin-prick pain. The device and methods can be used for stimulation of a single nerve fiber, groups of nerve fibers, nerve fibers of single type only as well as more the one type of nerve fibers simultaneously.

U.S. Pat. No. 5,150,704 to Tsuneo Tatebayashi et al. (hereinafter, "Tatebayashi et al.") titled "LASER THERAPEUTIC APPARATUS", issued Sep. 29, 1992, and is incorporated herein by reference. Tatebayashi et al. describe a laser therapeutic apparatus for treating a patient by irradiating selected body parts by laser beams generated by a plurality of laser probes.

U.S. Pat. No. 5,151,909 to Scott A. Davenport et al. (hereinafter, "Davenport et al.") titled "FREQUENCY DOUBLED SOLID STATE LASER HAVING PROGRAMMABLE PUMP POWER MODES AND METHOD FOR CONTROLLABLE LASERS", issued Sep. 29, 1992, and is incorporated herein by reference. Davenport et al. describe a laser system using non-linear crystals for second harmonic generation and solid-state gain media is operated under data processor control so that a plurality of pump power modes are available. The data processor modulates the pump power in a low power mode, and supplies continuous pump power in combination with Q-switching in a high power mode.

U.S. Pat. No. 4,215,694 to Viktor L. Isakov et al. (hereinafter, "Isakov et al.") titled "LASER THERAPY APPARATUS", issued Aug. 5, 1980, and is incorporated herein by reference. Isakov et al. describe a laser therapy apparatus including a radiating source, a control system of said radiating source, which system is connected to said source, a mechanical beam shifting scanner connected to said radiating source, a unit for processing and storing information on a program of exposing biological objects to irradiation, to whose output there is connected a unit control for reading out information from said information processing and storage unit, as well as an electromechanical unit whose outputs are connected to the mechanical beam shifting scanner, said electromechanical unit having a drive by means of which directional irradiation, i.e., the beam, is focused on an object exposed to irradiation and oriented in three spatial coordinates, one output of the control and information readout unit being connected to the input of the electromechanical unit, whereas its second output is connected to the input of the radiating source control system.

U.S. Pat. No. 7,329,251 to Tsuyoshi Yamada et al. (hereinafter, "Yamada et al.") titled "LASER TREATMENT APPARATUS", issued Feb. 12, 2008, and is incorporated herein by reference. Yamada et al. describe a laser treatment apparatus for performing treatment by irradiating an affected part with a laser beam that includes: a laser source capable of emitting beams of a plurality of different wavelengths; a first setting unit which sets an irradiation amount of a laser beam for treatment of a wavelength to be used for treatment; an emission amount changing unit which changes an emission amount of the beam in plural levels; an attenuating unit which attenuates the beam emitted by the laser source; and a control part which controls the emission amount changing unit and the attenuating unit based on the set irradiation amount of the treatment beam.

U.S. Pat. No. 6,066,127 to Hitoshi Abe (hereinafter, "Abe") titled "LASER TREATMENT APPARATUS", issued May 23, 2000, and is incorporated herein by reference. Abe describes a laser treatment apparatus which performs a medical or surgical treatment using laser-beam irradiation. The apparatus has a solid-state laser medium for obtaining a laser beam and an excitation light source for exciting the solid-state laser medium. The apparatus further has a first optical system having a Q-switch which emits light oscillated by the solid-state laser medium as a pulse wave laser beam, and a second optical system which emits the light oscillated by the solid-state laser medium as a continuous wave laser beam.

U.S. Pat. No. 6,312,451 to Jackson Streeter (hereinafter, "Streeter") titled "LOW LEVEL LASER THERAPY APPARATUS", issued Nov. 6, 2001, and is incorporated herein by reference. Streeter describes a low level laser therapy apparatus for treatment of various tissue injuries. In one embodiment, the apparatus includes a handheld laser probe coupled to a control unit for selecting and controlling laser energy dosage from about 1 joule/point to about 10 joules/point. The apparatus emits laser energy at a wavelength from about 630 nm to about 904 nm, with a mean power output of between about 100 mW to about 500 mW. The apparatus further includes an access control mechanism to limit operability to trained personnel.

U.S. Pat. No. 4,724,835 to Saul Liss et al. (hereinafter, "Liss et al.") titled "LASER THERAPEUTIC DEVICE", issued Feb. 16, 1988, and is incorporated herein by reference. Liss et al. describe a laser therapeutic apparatus that irradiates an area of cutaneous and/or subcutaneous physical injury, with a pulsed laser wave, producing healing and pain reduction.

U.S. Pat. No. 4,930,504 to Costas A. Diamantopoulos et al. (hereinafter, "Diamantopoulos et al.") titled "Device for biostimulation of tissue and method for treatment of tissue", issued Jun. 5, 1990, and is incorporated herein by reference. Diamantopoulos et al. describe a device for biostimulation of tissue including an array of substantially monochromatic radiation sources of a plurality of wavelengths, preferably of at least three different wavelengths.

U.S. Pat. No. 3,786,861 issued to Philip E. Eggers (hereinafter, "Eggers") on Jan. 22, 1974, titled "HEAT PIPES," and is incorporated herein by reference. Eggers describes a heat pipe having a fluid-tight container for transferring heat from a source adjacent to an evaporation region to a sink adjacent to a condenser region, a passage for transferring vapor from the evaporator region to the condenser region, and a wick having high heat conductivity for transferring condensate from the condenser region back to the evaporator region by capillary pumping and for conducting heat from the container in the evaporator region to the evaporation sites and from the condensation sites to the container in the condenser region.

U.S. Pat. No. 7,124,810 issued to Hsin-Ho Lee et al. (hereinafter, "Lee et al.") on Oct. 24, 2006, titled "HEAT PIPE HAVING WICK STRUCTURE", and is incorporated herein by reference. Lee et al. describe a heat pipe that includes a pipe, a wick formed on an inner wall of the pipe, and a working fluid sealed in the pipe and soaked in the wick. The wick is formed by sintering nano-size metal powder disposed inside the pipe.

U.S. Pat. No. 5,913,884 issued to Kenneth Trauner et al. (hereinafter, "Trauner et al.") on Jun. 22, 1999, titled "INHIBITION OF FIBROSIS BY PHOTODYNAMIC THERAPY", and is incorporated herein by reference. Trauner et al. describe a method for modulating wound healing in a mammal. The method includes the steps of: (a) administering a photosensitizer to a mammal that has an unhealed or partially-healed wound; (b) waiting for the photosensitizer to reach an effective tissue concentration at the wound site; (c) photoactivating the photosensitizer by delivering specifically to the wound site light of an effective wavelength and intensity, for an effective length of time. The modulation of wound healing can include hastening healing by administering a low dose of photodynamic therapy.

There remains a need for an improved apparatus and method for managing chronic pain, particularly chronic pain management using optical nerve-stimulation signals, and using heat to provide therapy to surrounding tissues.

SUMMARY OF THE INVENTION

In some embodiments, the present invention provides an apparatus that includes an infrared-light nerve stimulation-plus-therapeutic-heat (INS-plus-TH) device configured to be implanted in an animal, wherein the INS-plus-TH device includes: a plurality of light sources that output infrared-light signals that are efficacious for nerve stimulation, wherein the light sources generate heat; a controller operatively coupled to control the plurality of light sources; and a plurality of thermally conductive material extensions that lead away from the INS-plus-TH device and spread the heat into surrounding tissue of the animal and away from at least one of the group consisting of the light sources and the controller.

In some embodiments, the present invention provides a method for providing infrared-light nerve stimulation-plus-therapeutic-heat (INS-plus-TH), the method including providing a plurality of light sources configured to emit infrared-light nerve-stimulation signals; providing a plurality of thermally conductive extensions configured to transfer heat generated by the plurality of light sources away from the plurality of light sources; implanting the plurality of light sources and the plurality of thermally conductive extensions into an animal; emitting a plurality of infrared-light nerve-stimulation signals toward neural tissue of the animal from the plurality of light sources, wherein the emitted infrared-light nerve-stimulation signals are configured to generate action potentials in the neural tissue of the animal, and wherein the emitting of the plurality of infrared-light nerve-stimulation signals includes generating heat; controlling the emitting of the plurality of infrared-light nerve-stimulation signals to generate action potentials in the neural tissue; and transferring the heat generated by the plurality of light sources during the emitting of the plurality of infrared-light nerve-stimulation signals away from the plurality of light sources and into surrounding tissue of the animal using the plurality of thermally conductive extensions.

BRIEF DESCRIPTION OF THE FIGURES

Each of the items shown in the following brief description of the drawings represents some embodiments of the present invention.

FIG. 2A is a schematic diagram 200 showing electrical stimulation (ES) applied to a rat sciatic nerve.

FIG. 2B is a schematic diagram 201 showing the infrared nerve stimulation (INS) of a rat sciatic nerve.

FIG. 5 is a schematic perspective view of an INS-plus-therapeutic-heat device 501.

FIG. 6 is a graph of a temperature (° C.)-versus-distance (X) thermal analysis 601.

FIG. 7A is a schematic perspective view of an INS-plus-therapeutic-heat system 701.

FIG. 7B is a schematic perspective view of INS-plus-therapeutic-heat device 702 shown in FIG. 7A.

FIG. 8A is a table 801 of pulse-signal characteristics associated with a computer simulation of a plurality of aperture sizes for an infrared-light nerve-stimulation device.

FIG. 8B is a graph 802 of the simulated penetration depth versus pulse-energy-per-penetration-depth according to the data in table 801.

FIG. 8C is a graph 803 showing isotemperature contour lines of the simulated temperature profiles resulting from different aperture diameters versus penetration depth according to the data in table 801.

FIG. 9A is a graph 901 showing isotemperature contour lines of simulated temperature profiles in a tissue resulting from a simulated exposure to a ten-second-duration pulse train (at a 15-Hz pulse-repetition rate) from an infrared-light nerve stimulation device having a 600-μm aperture.

FIG. 9B is a graph 902 showing the simulated temperature change (delta T in degrees Celsius) one millimeter under the tissue surface versus time (seconds).

FIG. 9C is a table 903 showing the pulse-signal characteristics associated with a computer simulation of the 600-μm aperture.

FIG. 9D is a table 904 showing the physical characteristics of the tissue being stimulated during the computer simulation of the 600-μm aperture.

FIG. 10A is a graph 1001 showing isotemperature contour lines of simulated temperature profiles in a tissue resulting from a simulated exposure to a ten-second-duration pulse train (at a 15-Hz pulse-repetition rate) from an infrared-light nerve stimulation device having a 400-μm aperture.

FIG. 10B is a graph 1002 showing the temperature of the tissue surface (degrees Celsius) versus time (seconds).

FIG. 10C is a table 1003 showing the pulse-signal characteristics used in a computer simulation of stimulation light from a 400-μm aperture at a surface irradiance having a value of about 0.52 J/cm$^2$.

FIG. 10D is a table 1004 showing the physical characteristics of the tissue being simulated with light stimulation from a 400-μm aperture (and an irradiance of 0.52 J/cm$^2$).

FIG. 11A is a graph 1101 showing isotemperature contour lines of simulated temperature profiles in a tissue resulting from a simulated exposure to a ten-second pulse train (at a 9-Hz pulse-repetition rate) from an infrared-light nerve stimulation device having a 400-μm aperture.

FIG. 11B is a graph 1102 showing the maximum temperature of the tissue surface (in degrees Celsius) versus time (in seconds) for a pulse train of 2.5 millisecond pulses each having 1.04 mJ.

FIG. 11C is a table 1103 showing the pulse-signal characteristics used in a computer simulation of stimulation light from a 400-μm aperture at a surface irradiance having a value of about 0.8 J/cm$^2$.

FIG. 11D is a table 1104 showing the physical characteristics of the tissue being stimulated with light stimulation from the 400-μm aperture (and an irradiance of 0.8 J/cm$^2$).

FIG. 11E is a graph 1105 of temperature down the center of the aperture (degrees Celsius) versus depth (meters).

FIG. 12A is a graph 1201 showing isotemperature contour lines of simulated temperature profiles in a tissue resulting from a simulated exposure to a ten-second pulse train from an infrared-light nerve stimulation device having a 400-μm aperture and three channels having one-millimeter (1-mm) spacing between each channel.

FIG. 13A1 is another diagram of INS-plus-therapeutic-heat device 702 of FIG. 7B.

FIG. 13A2 is a simulated temperature profile 1301 for an external-cuff-stimulation device such as INS-plus-therapeutic-heat device 702 of FIG. 7B.

FIG. 13A3 is detailed schematic diagram of INS-plus-therapeutic-heat unit 703A used for some embodiments of upper cuff portion 703 of FIG. 7B and FIG. 13A1.

FIG. 13A4 is detailed schematic diagram of INS-plus-therapeutic-heat unit 703B used for some embodiments of upper cuff portion 703 of FIG. 7B and FIG. 13A1.

FIG. 13B is a table 1302 showing the pulse-signal characteristics associated with a computer simulation of the temperature profile 1301.

FIG. 13C is a table 1303 showing the physical characteristics of the tissue being stimulated during the computer simulation of the temperature profile 1301.

FIG. 16A is a simulated temperature profile 1601 conducted for a penetrating array nerve stimulation system 1602.

FIG. 16B is a magnified view of simulated temperature profile 1601 showing the simulated temperature profile near system 1602.

FIG. 16C is a table 1603 showing the pulse-signal characteristics associated with simulated computer simulation of temperature profile 1601.

FIG. 16D is a table 1604 showing the physical characteristics of the simulated tissue being stimulated during the computer simulation of the temperature profile 1601.

FIG. 16E is a graph 1605 showing the maximum temperature down the center of the aperture (degrees Celsius) versus time (seconds).

DETAILED DESCRIPTION OF THE INVENTION

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

As used herein, an optical signal (the signal) is light (of any suitable wavelength including ultraviolet and infrared wavelengths as well as visible wavelengths) of a signal wavelength being amplified, or of a laser output (and may or may not be modulated with information).

The Biology of Pain Management

Figure 1A:
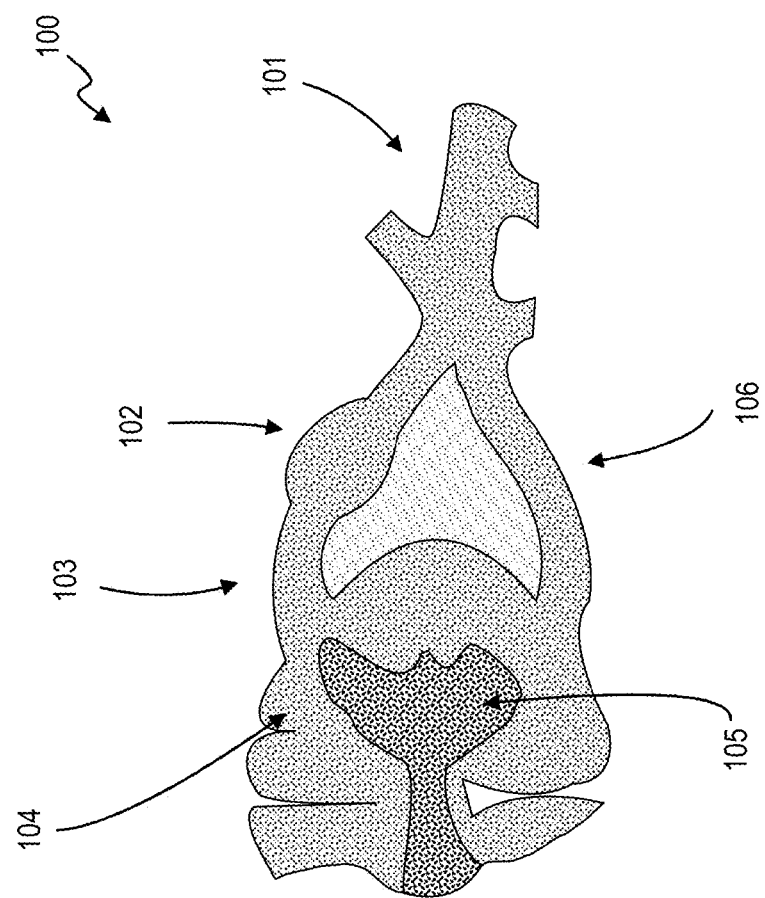
FIG. 1A is a cross-section view of a spinal cord 100 of an animal.

FIG. 1A is a cross-section view of a spinal cord 100 of an animal. Receptors in the body (e.g., in the skin or other organ or tissue) send information to spinal cord 100 through the spinal nerves 101. The cell bodies for these nerve fibers 101 are located in the dorsal root ganglion 102. The nerve fibers 101 enter the spinal cord 100 through the dorsal root 103. Some fibers make synapses with other neurons in the dorsal horn 104, while others continue up to the brain (sensory fibers converge in dorsal horn 104 of spinal cord 100, which is one end of the spinal-thalamic tract (STT) that passes pain information to the brain). Many cell bodies in the ventral horn 105 of the spinal cord 100 send axons through the ventral root 106 to muscles to control movement.

Figure 1B:
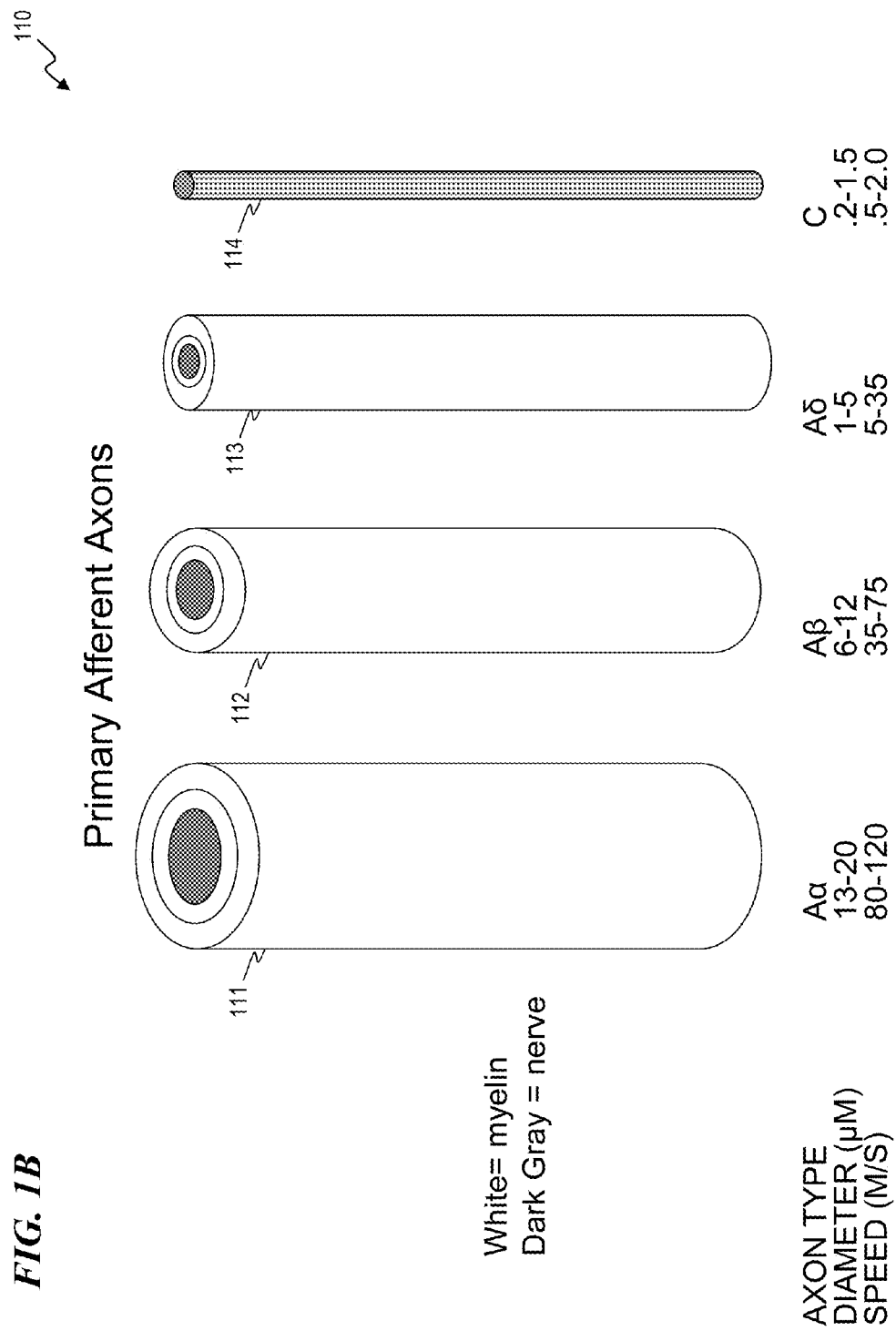
FIG. 1B is a diagram that illustrates the types of primary afferent axons 110.

FIG. 1B is a diagram that illustrates the types of primary afferent axons 110. As used herein, an axon is a long, slender projection of a nerve cell, or neuron that conducts electrical impulses away from the neuron's cell body or soma. As used herein, afferent neurons (e.g., afferent axons) carry nerve impulses from receptors or sense organs towards the central nervous system. Aα axons 111 are the largest sensory fibers, but are not relevant for pain. Aβ axons 112 carry touch information, and are the largest, most heavily myelinated fibers that play a role in pain processing. Aδ axons 113 and C axons 114 carry different aspects of pain sensing. Aδ axons 113 are slightly myelinated, while C axons 114 have no myelination.

Figure 1C:
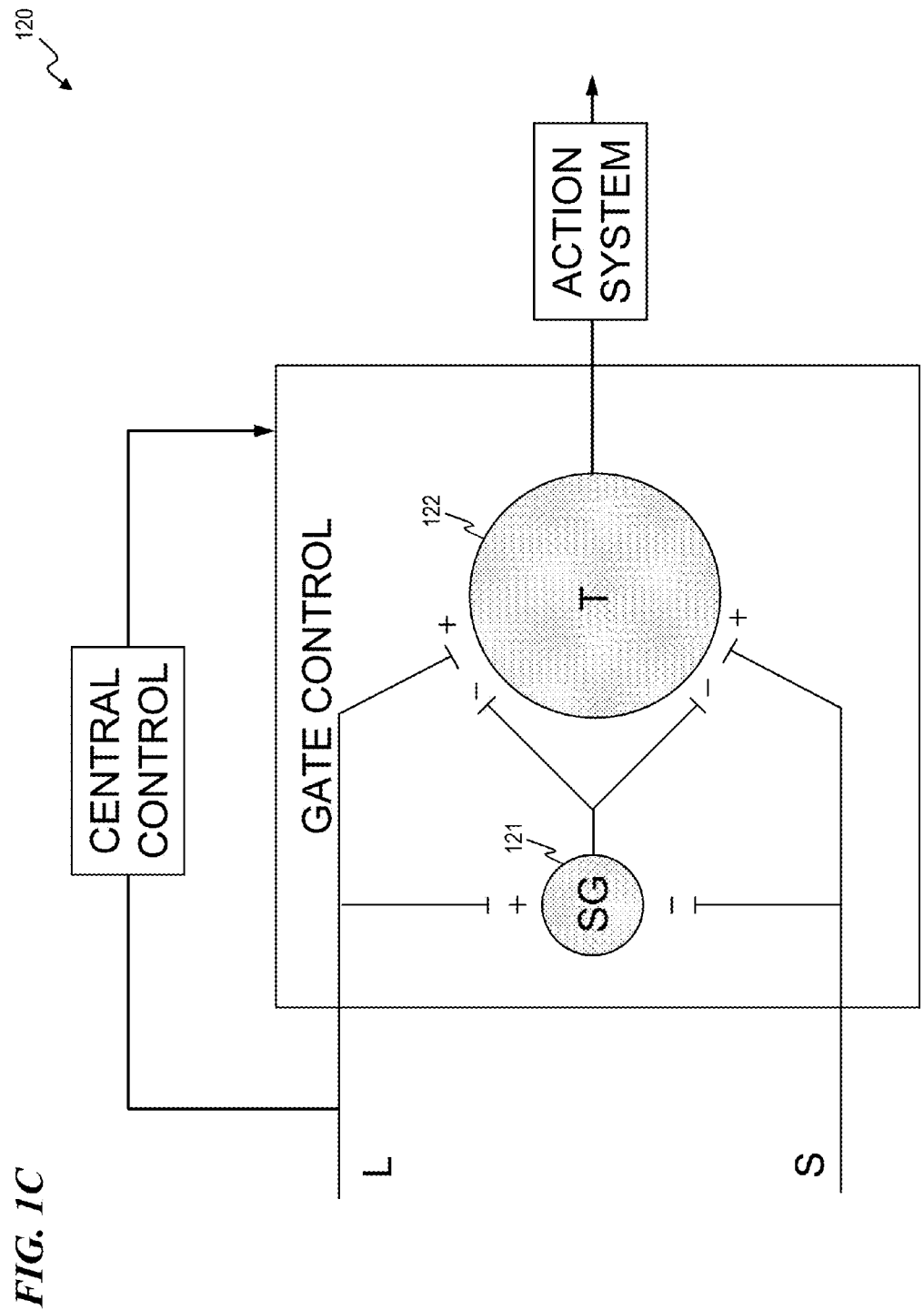
FIG. 1C is a schematic diagram of the "Gate Theory" 120 of neuro-modulation for pain management.

FIG. 1C is a schematic diagram of the "Gate Theory" 120 of neuro-modulation for pain management. Large-diameter (L in FIG. 1C (e.g., Aβ fibers)) and small-diameter (S in FIG. 1C (e.g., Aδ and C fibers)) primary afferent fibers project to the substantia gelatinosa (SG) 121 and second order transmission (T) neurons 122 in the spinal dorsal horn 104. The inhibitory effect of SG 121 neuronal activity is increased by L fiber activity and decreased by S fiber activity. T neurons 122 transmit information to the brain and other action sites.

Figure 1D:
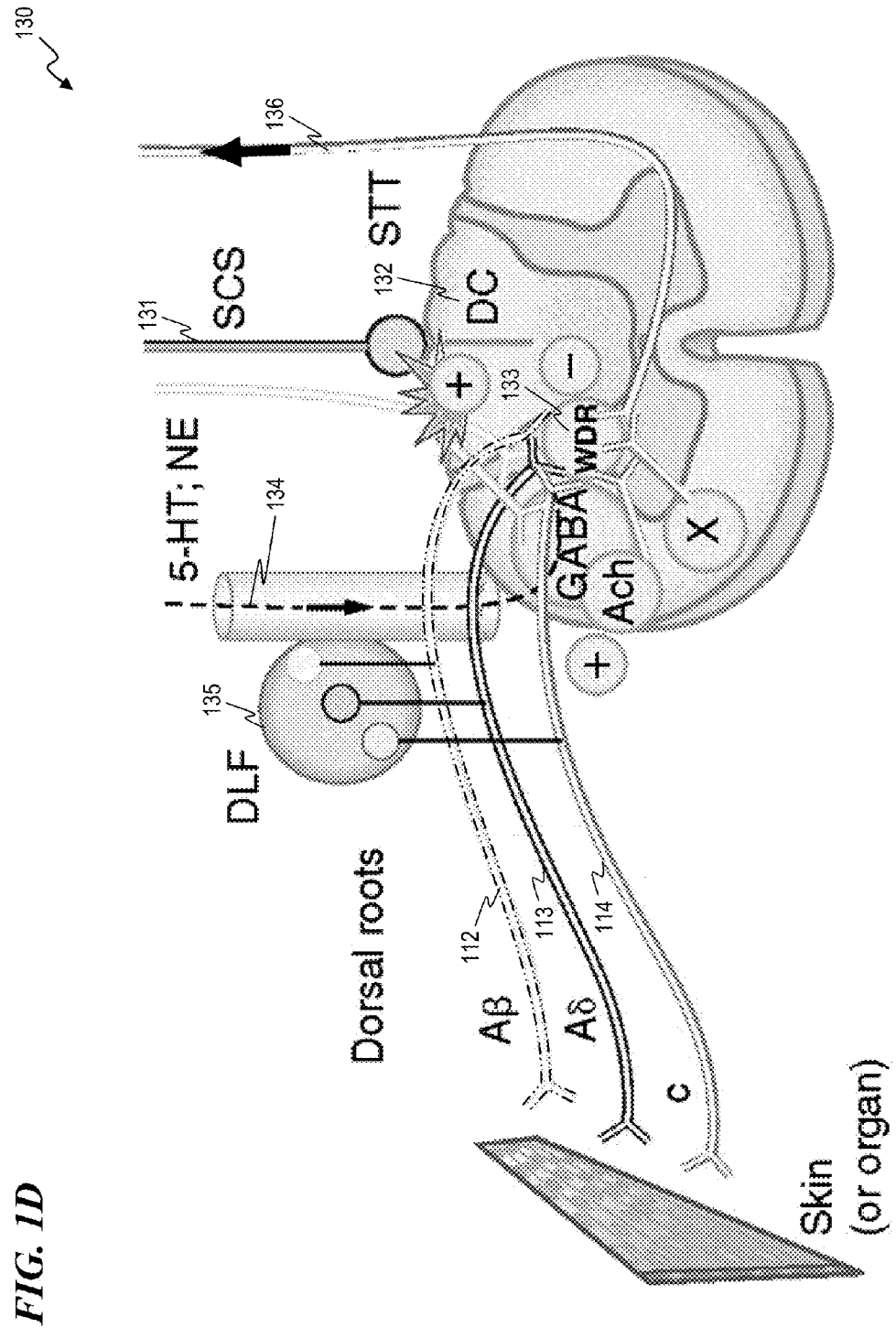
FIG. 1D is a schematic diagram of mechanisms and neurotransmitters 130 involved in the effects of spinal-cord stimulation (SCS) in neuropathic pain.

FIG. 1D is a schematic diagram of mechanisms and neurotransmitters 130 involved in the effects of spinal-cord stimulation (SCS) in neuropathic pain (see Figure 95.1 in Bonica's *Management of Pain*, Ballantyne, Jane C., Fishman, Scott M., Rathmell, James P., Chapter 95: Spinal Cord Stimulation, Page 1381, Lippincott Williams & Wilkins, 2009). Mechanisms and neurotransmitters 130 include ascending and descending control paths, a variety of excitatory and inhibitory neurotransmitters released by different nerve types, and wide dynamic range neurons (WDR) that receive input from all sensory fibers and ascending and descending control paths. SCS activation 131 of dorsal column collaterals 132 secondarily induces release of gamma-aminobutyric acid (GABA) from dentate-hilus (DH) interneurons, activating mainly GABA-B receptors and decreasing the release of excitatory amino acids from hyperexcited second-order DH WDR neurons 133. SCS 131 also causes cholinergic neurons to activate M4 and M2 muscarinic-type receptors (e.g., acetylcholine (Ach)). Several other transmitters, adenosine and hitherto unknown substances are also likely involved. Furthermore, the orthodromic SCS-induced activity in the dorsal columns 132 might—via neuronal circuitry in the brain stem (or even more rostrally)—induce descending inhibition via serotonergic (e.g., 5-hydroxytryptamine (5-HT)) and noradrenergic (NE) pathways 134 in the dorsolateral funiculus (DLF) 135, which might contribute to inhibitory influences in the DHs. DC, dorsal columns 132; STT, spinothalamic tract 136. In some embodiments, SCS and transcutaneous electrical nerve stimulation (TENS) acts through other means besides just stimulation of Aβ fibers.

Pain Management Modalities

Transcutaneous electrical nerve stimulation (TENS):
Electrodes placed on skin surface, generally near site of pain
Effective (with respect to previous rule of thumb) for acute pains such as:
 orafacial;
 post-operative;
 angina pectoris;
 peripheral neuropathic pain ("best" indication);
 diabetic neuropathies;
 post-trauma; and
 failed back surgery.
Peripheral Nerve Stimulation (PNS):
 stimulate dorsal roots to mimic SCS without penetrating vertebral discs;
 can also be placed more distally away from cord; and
 works best for similar indications as tens, especially peripheral neuropathies.
A successful trial of TENS or a nerve block is strong indicator that an implanted PNS would work well for a patient.

Figure 1E:
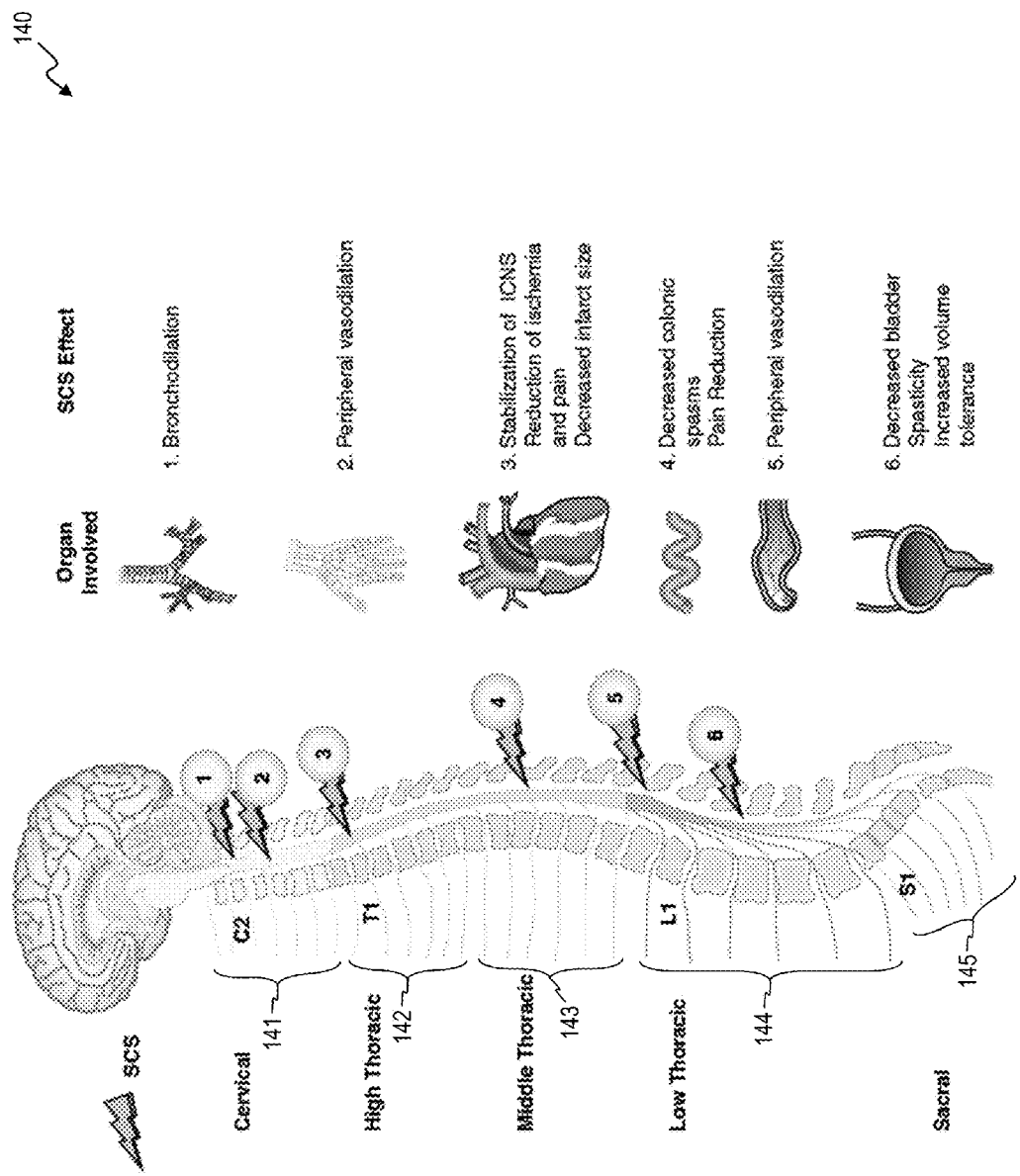
FIG. 1E is a schematic diagram of Spinal Cord Stimulation (SCS) characteristics 140.

FIG. 1E is a schematic diagram of spinal cord stimulation (SCS) characteristics 140. In some embodiments, for SCS, electrode leads are placed inside vertebral discs, but outside dural membranes at appropriate heights along the spinal column for target area of pain. The most common uses for SCS include: chronic neuropathic pain, chronic low back pain, refractory angina pectoris (chest pains), interstitial cystitis (inflammation around bladder) and other visceral pains, and complex regional pain syndrome. In some embodiments, the effect of SCS directed toward the cervical spine 141 includes bronchodilation and peripheral vasodilation. In some embodiments, the effect of SCS directed toward the high thoracic spine 142 includes stabilization of intercostals nerves (ICNs), reduction of ischemia and pain, and decreased infarct size. In some embodiments, the effect of SCS directed toward the middle thoracic spine 143 includes decreased colonic spasms, and pain reduction. In some embodiments, the effect of SCS directed toward the low thoracic spine 144 includes peripheral vasodilation. In some embodiments, the effect of SCS directed toward the sacral spine 145 includes decreased bladder spasticity, increased bladder volume, and increased bladder tolerance.

Deep Brain Stimulation (DBS) generally involves placing electrodes in sensory portions of the thalamus, though motor and pre-frontal cortex can also be a target.

Most successful indications:
 central neuropathic pain, especially from degeneration of spinal cord neurons; and
 peripheral neuropathic pain not responding to PNS or SCS FIG. 2A is a schematic diagram 200 showing electrical stimulation (ES) applied to a rat sciatic nerve. In some embodiments, the objective of the ES is the generation of compound-nerve-action potentials (CNAPs) in the gastrocnemius fascicle 210G. In some embodiments, a CNAP-versus-time plot 200G represents the CNAP generation in fascicle 210G caused by ES of the sciatic nerve. CNAP-versus-time plot 200B shows that ES devices lack the specificity to target the neurons responsible for pain without also activating other sensory or motor neurons as a side effect (e.g., in some embodiments, in addition to generating desired CNAPs in fascicle 210G, ES of the rat sciatic nerve also generates CNAPs in the biceps femoris fascicle 210B).

FIG. 2B is a schematic diagram 201 showing the infrared nerve stimulation (INS) of a rat sciatic nerve. In some embodiments, the objective of the INS is to generate CNAPs in fascicle 210G. In some embodiments, a CNAP-versus-time plot 201G represents the CNAP generation in fascicle 210G caused by INS of the sciatic nerve. Unlike ES, INS provides specific simulation such that substantially zero CNAPs are generated in non-targeted sensory or motor neurons (e.g., in some embodiments, as shown in CNAP-versus-time plot 201B, substantially zero CNAPs are generated in fascicle 210B by INS of the rat sciatic nerve).

Infrared nerve stimulation (INS) provides more precise neural stimulation compared to electrical stimulation (ES) methods because light is directed in a single direction, it has no stimulation artifact, and the various materials for implantable INS designs can be safer and more biocompatible than current ES devices.

In some embodiments of the present invention, the preferred target neural tissue for pain relief therapy using either INS or therapeutic heat or both INS and therapeutic heat is the peripheral nervous system, especially: ulnar, median, radial, and other nerves in the arm (neuropathic pain, carpal tunnel, tennis elbow, etc.); femoral, sural, sciatic, and other nerves in the leg (neuropathic pain); and occipital nerve in the neck region (migraines). The first two sets of nerves can treat neuropathic pain arising from nerve injury, while the latter may be effective in treating migraines.

In some embodiments of the present invention, potential target applications include: lumbar dorsal roots for lower back pain; sacral root for interstitial cystitis as well as incontinence; trigeminal nerve for facial neuralgia; vagus nerve for chronic angina, as well as obesity treatment, epilepsy treatment, and depression treatment; spinal cord stimulator for variety of neuropathic conditions; and a deep brain stimulator for a variety of neuropathic conditions.

Figure 3A:
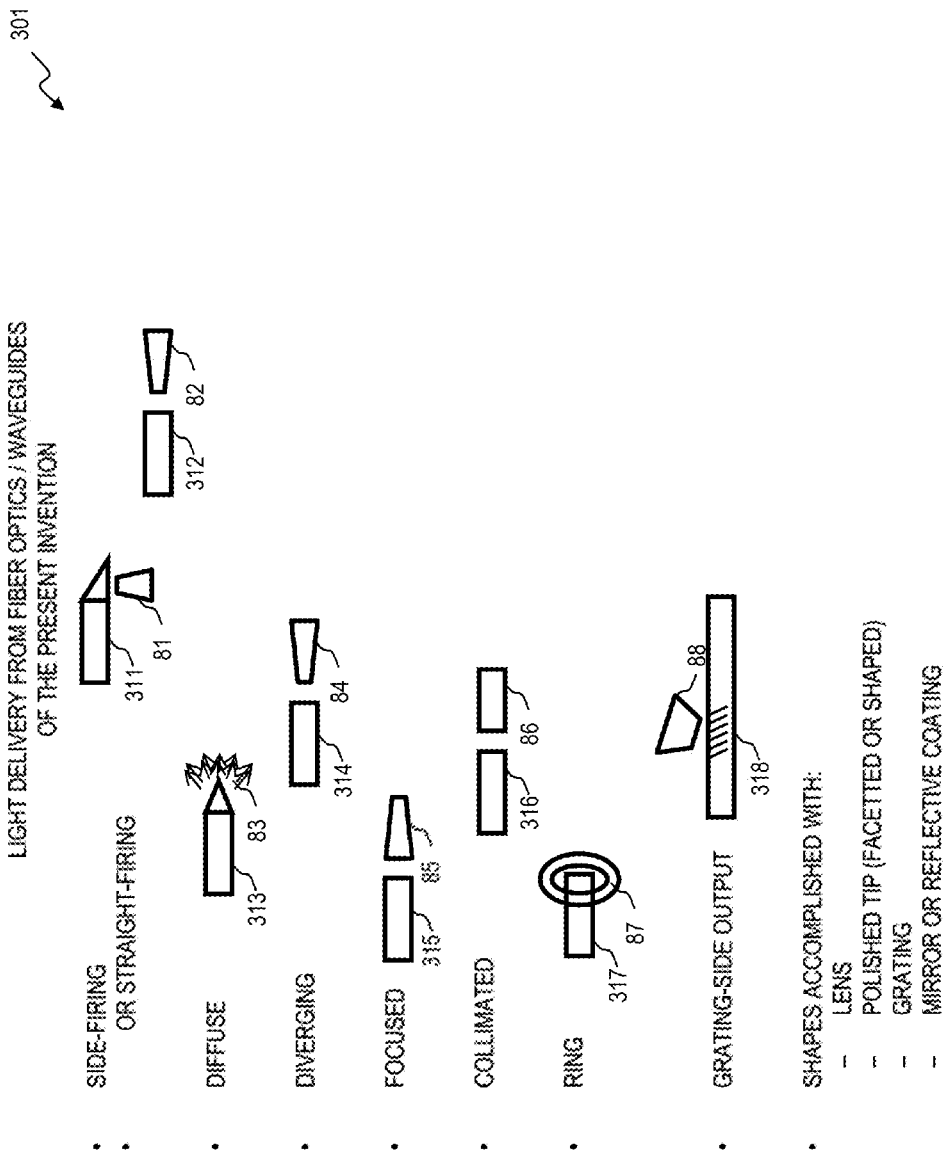
FIG. 3A is a schematic drawing of a plurality of light-delivery options 301 from fiber optics/waveguides.

FIG. 3A is a schematic drawing of a plurality of light-delivery options 301 from fiber optics/waveguides. In some embodiments, the shape of the laser beam delivered by the fiber is accomplished with a lens, polished tip (facetted or shaped), grating, mirror or reflective coating, or some combination of the above. Waveguide 311 ends in an angled facet and/or fiber-Bragg grating that reflects or diffracts the light out in a radial or side ("side firing") direction relative to the light-propagation axis of the waveguide as laser beam 81. Waveguide 312 ends in an end facet that transmits the light out in an axial direction relative to the light-propagation axis of the waveguide, as laser beam 82. Waveguide 313 ends in a conical (as shown), rough or ground "frosted" end that diffuses the light out in a generally axial direction relative to the light-propagation axis of the waveguide as laser beam 83. Waveguide 314 ends in a lens-type end facet that transmits and diverges the light out in an axial direction relative to the light-propagation axis of the waveguide as laser beam 84. Waveguide 315 ends in a lens-type end facet that transmits and focuses the light out in an axial direction relative to the light-propagation axis of the waveguide as laser beam 85. Waveguide 316 ends in a lens-type end facet that transmits and collimates the light out in a parallel beam in an axial direction relative to the light-propagation axis of the waveguide as laser beam 86. Waveguide 317 ends in an annular lens-type end facet that transmits and focuses the light out in a conical ring centered about an axial direction relative to the light-propagation axis of the waveguide as laser beam 87. In some such embodiments, the very end facet is polished and coated with a metallic or dielectric-layered reflective structure to better facilitate the ring-shaped output beam 87. Waveguide 318 has a mid-fiber or end-fiber grating that disperses light of a selected wavelength in a radial direction from the side of the fiber of the waveguide as laser beam 88. In some embodiments, a combination of two or more of such features as shown in fiber ends 311, 312, 313, 314, 315, 316, 317 and/or 318 are applied to a single fiber tip to provide a hybrid beam shape combining some aspects of beams 81, 82, 83, 84, 85, 86, 87 and/or 88, respectively. In some embodiments, a bundle having a plurality of such fibers and ends are used in combination to get a plurality of beams and/or a plurality of beam shapes in a small area. In some embodiments, the ends of the plurality of fibers terminate at a plurality of different axial lengths to provide output beams that leave the bundle at different points along the length of the fiber bindle.

Figure 3B:
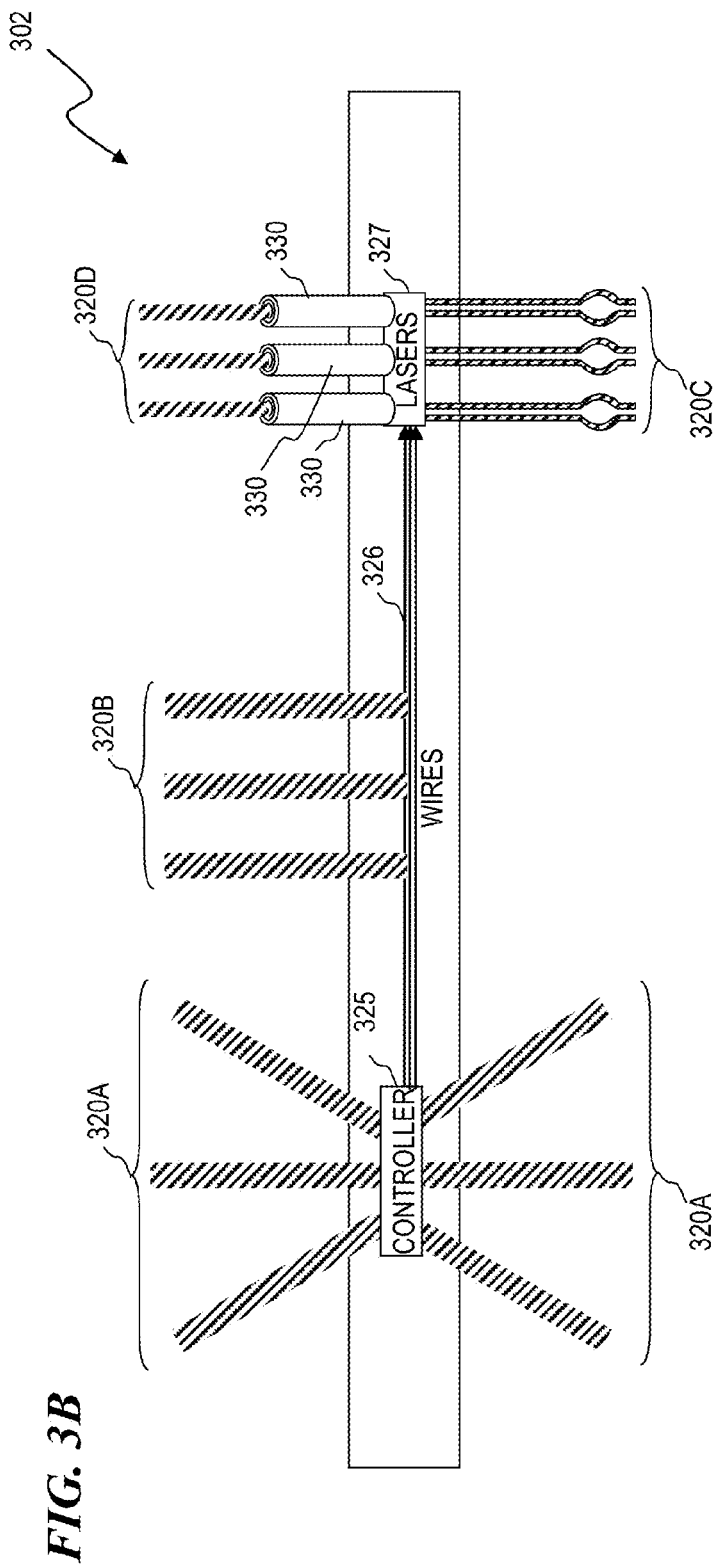
FIG. 3B is a schematic drawing of heat removal configurations for an optical-stimulation-plus-therapeutic heat system 302.

FIG. 3B is a schematic drawing of various heat-removal configurations for an optical-stimulation-plus-therapeutic heat system 302. In some embodiments, system 302 includes one or more lasers 327 (e.g., in some embodiments, a plurality of VCSELs 327) configured to optically stimulate a tissue of an animal in order to generate nerve-action-potentials (NAPs) in the tissue, a controller 325 operatively coupled to lasers 327 and configured to control lasers 327, and one or more wires 326 configured to operatively connect controller 325 to lasers 327. In some embodiments, a plurality of heat-transfer structures 320 (e.g., 320A, 320B 320C, and/or 320D) are operatively coupled to each of one or more of the controller 325, wires 326, and lasers 327. In other embodiments, heat-transfer structures 320 are connected to lasers 327 only. In still other embodiments, heat-transfer structures 320 are connected to any other suitable combination of controller 325, wires 326, and lasers 327. In some embodiments, each heat-transfer structure 320 includes a wire containing copper or other suitable material having a high thermal conductivity. In some embodiments, heat-transfer structures 320 include heat-transfer fins. In some embodiments, heat-transfer structures 320 include carbon nanotube (CNT) materials.

In some embodiments, heat-transfer structures 320 include heat pipes (e.g., in some embodiments, the heat-transfer structures include heat pipes such as described by U.S. Pat. No. 3,786,861 to Philip E. Eggers, titled "HEAT PIPES", issued Jan. 22, 1974, and U.S. Pat. No. 7,124,810 to Hsin-Ho Lee et al., titled "HEAT PIPE HAVING WICK STRUCTURE", issued Oct. 24, 2006, both of which are incorporated herein by reference). In some embodiments, heat-transfer structures 320 are coated with a bio-compatible material (e.g., a bio-compatible material such as provided by Hydromer, Inc., 35 Industrial Parkway, Branchburg, N.J. 08876) such that system 320 can be safely implanted in the tissue of the animal to be stimulated.

In some embodiments, heat-transfer structures 320 are coupled to their respective heat source (e.g., controller 325) in a configuration 320a such that the individual heat-transfer structures 320 at a given heat source are coupled to that heat source at a plurality of angles (e.g., in some embodiments, configuration 320a includes some heat-transfer structures 320 that are coupled to controller 325 at perpendicular angles and some that are coupled to controller 325 at non-perpendicular angles). In some embodiments, heat-transfer structures 320 are coupled to their respective heat source (e.g., wires 326) in a configuration 320b such that each of the individual heat-transfer structures 320 at a given heat source are coupled to that heat source at substantially the same angle (e.g., perpendicular to the heat source). In some embodiments, heat-transfer structures 320 are coupled to multiple sides of an individual heat source (e.g., see heat-transfer structures 320 coupled to controller 325), and in other embodiments, heat-transfer structures 320 are only coupled to a single side of an individual heat source (e.g., see heat-transfer structures 320 coupled to wires 326). In some embodiments, heat-transfer structures 320 include "spider-cuff" configurations 320c. In some embodiments, heat-transfer structures 320 are coupled to their respective heat source in an insulated configuration 320d such that at least a portion of heat-transfer structures 320 include insulation layers 330. In some such embodiments, insulation layers 330 are configured such that the heat removed from lasers 327, wires 326, and/or controller 325 is spread into the surrounding tissue at a predetermined distance away from lasers 327, wires 326, and/or controller 325.

Figure 4:
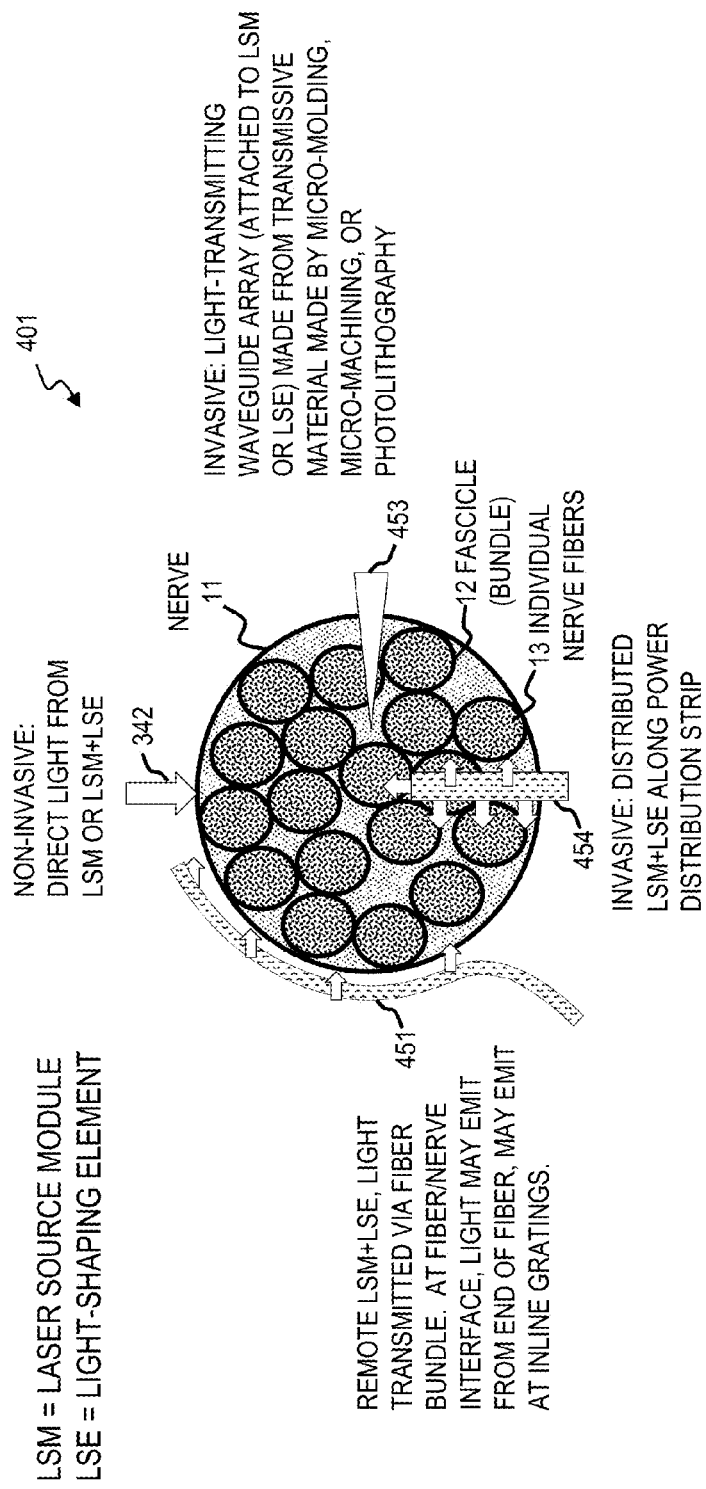
FIG. 4 is a schematic representation of a plurality of nerve stimulator light delivery options 401, according to some embodiments of the present invention.

FIG. 4 is a schematic representation of a plurality of nerve stimulator light delivery options 401, according to some embodiments of the present invention. In some embodiments, the present invention provides a plurality of light-delivery techniques for stimulating nerve 11, specific fascicle 12 (i.e., a specific bundle of nerve fibers 12) within the nerve 11, or even a specific individual nerve fiber 13 within the fascicle 12 in the peripheral nervous system (PNS) and/or the central nervous system (CNS), including cranial nerves, of an animal. In some embodiments, the light-delivery technique is non-invasive to the nerve 11, fascicle 12, and/or nerve fiber 13 because the light-delivery technique does not penetrate the surface of the nerve 11. In some other embodiments, the light-delivery technique is considered invasive to the nerve 11 because waveguides, optical-electrodes, and/or the like penetrate the outer surface of the nerve 11 in order to provide stimulation of fascicles 12 or nerve fibers 13 that are located on the interior of the nerve 11. In some embodiments of the present invention, the pain-relief therapy by therapeutic heat and/or optical INS is enhanced by also including nerve stimulation or preconditioning by electrical signals along with the infrared optical nerve-stimulation signals, such as described in U.S. patent application Ser. No. 12/573,848 (which issued as U.S. Pat. No. 8,160,696 on Apr. 17, 2012) titled "NERVE STIMULATOR AND METHOD USING SIMULTANEOUS ELECTRICAL AND OPTICAL SIGNALS," which is incorporated herein by reference.

In some embodiments, a non-invasive direct-light technique is used to stimulate a nerve 11, fascicle 12, and/or nerve fiber 13, or a combination of a nerve 11, fascicle 12, and/or nerve fiber 13 using laser-light beam 452. In some embodiments, non-invasive direct-light technique provides a laser-light beam 452 from a laser-source module (LSM) and/or light-shaping element (LSE), as described above for FIG. 2, to stimulator the nerve 11, fascicle 12, and/or nerve fiber 13. In some embodiments, remote LSM and/or LSE is used to stimulate one or more areas of nerve 11, fascicle 12, and/or nerve fiber 13, wherein light is transmitted via a fiber bundle 451 at the fiber 351/nerve 11 interface, wherein, in some embodiments, the light is emitted from the end of fiber bundle 451 and/or light is emitted from multiple locations along the fiber bundle 451 using inline fiber gratings. In some embodiments, an invasive method is used to stimulate the nerve 11 using a light-transmitting waveguide array 453 implanted into nerve 11, fascicle 12, and/or nerve fiber 13 (attached to LSM or LSE) and formed from light-transmissive material made by micro-molding, micro-machining, and/or photolithography. In some other embodiments, an additional invasive method is used to stimulate the nerve 11 by implanting a power distribution strip 454 that includes a plurality of light emitting devices that are each capable of stimulating nerve 11, fascicle 12 and/or individual nerve fiber 13. In some embodiments, a combination of light delivery options are used to stimulate nerve 11, fascicle 12, and/or nerve fiber 13 (i.e., in some embodiments, a combination of one or more of the described techniques, including, laser-light beam 452, fiber bundle 451, waveguide array 453, and/or power-distribution strip 454 are used for stimulating nerve 11, fascicle 12, and/or nerve fiber 13).

INS Plus Therapeutic Heat

In some embodiments, the present invention provides a method and apparatus for pain management that routes the heat generated from the (optical stimulation) laser source(s) away from the laser sources to both minimize the heat load on the nerve and to use the heat in a therapeutic manner to improve healing, reduce inflammation, and other suitable therapies. In other embodiments, the heat transferred away from the laser sources is used primarily to minimize heat load (e.g., prevent thermal damage to tissue near the optical sources or to the INS optical-output devices themselves), and only infrared nerve stimulation (INS) from the laser sources is used to reduce pain. In some embodiments, highly thermally conductive material extensions (e.g., wires, tubes, heat pipes or the like) spread the heat away from the laser sources. In some embodiments, the extension wires are flexible in order to make the patient more comfortable. In some such embodiments, an INS-plus-therapeutic-heat device has a "Spider Cuff" design (see FIG. 5).

In some embodiments, the core material of the heat-transfer extensions is a wire containing copper or other suitable material having a high thermal conductivity. In some embodiments, the core and/or coating material of the heat-transfer extensions include carbon nanotube (CNT) materials. In some embodiments, the extension wires are coated with a bio-compatible material to make them bio-compatible.

FIG. 5 is a schematic perspective view of an INS-plus-therapeutic-heat device 501. In some embodiments, laser sources 505 are centrally located in device 501 and flexible extension wires 510 protrude away from laser sources 505 in a plurality of directions. In some embodiments, extension wires 510 are configured to transfer heat away from laser sources 505 during the operation of device 501.

FIG. 6 is a graph of a temperature (° C.)-versus-distance (X) thermal analysis 601 showing that a 2° C. maximum temperature rise of an implanted INS-plus-therapeutic-heat device is achievable in some embodiments of the present invention. In some embodiments of the devices of the present invention, the limit allowed for the maximum temperature rise of the outside of the device adjacent the patient's tissue is 2° C. This 2° C. limit for an implanted medical device is a standard set by ISO 14708 (a standard set forth by the International Organization for Standardization), which is titled "Implants for Surgery—Active Implantable Medical Devices" (which states "No outer surface of an implantable part of the active implantable medical device shall be greater than 2° C. above the normal surrounding body temperature of 37° C. when implanted, and when the active implantable medical device is in normal operation or in any single-fault condition."). In other embodiments of the present invention, other temperature-rise limits are used.

FIG. 7A is a schematic perspective view of an INS-plus-therapeutic-heat system 701. In some embodiments, system 701 includes an INS-plus-therapeutic-heat device 702 that is implanted in a human person 99 at or near the spinal cord 97 (connected to brain 95) of person 99.

FIG. 7B is a schematic perspective view of INS-plus-therapeutic-heat device 702 shown in FIG. 7A. In some embodiments, device 702 includes a vertical-cavity-surface-emitting laser (VCSEL) array 705 and one or more heat spreaders 710 operatively coupled to array 705 and configured to spread heat generated by array 705 away from array 705 and into surrounding tissue of person 99. In some embodiments, array 705 and heat spreaders 710 are contained within a silicone body 706. In other embodiments, array 705 and heat spreaders 710 are contained within a body that is made of any other suitable material (e.g., a bio-compatible material such as provided by Hydromer, Inc., 35 Industrial Parkway, Branchburg, N.J. 08876). In some embodiments, device 702 includes an upper cuff portion 703 that is placed on a first side of a peripheral nerve 98 of person 99, and a lower cuff portion 704 that is placed on a second, opposite side of peripheral nerve 98. In some such embodiments, cuff portion 703 and cuff portion 704 both include a VCSEL array 705, one or more heat spreaders 710 operatively coupled to array 705, and a silicone body 706 that contains the array 705 and the heat spreaders 710.

Optimizing Aperture Size

In some embodiments, in order to determine the key characteristics (pulse-repetition rate, pulse energy, channel spacing, and other suitable characteristics) for an infrared-nerve stimulation (INS) pain-management implant, and to investigate the feasibility of various approaches (examining temperature changes) numerical simulations were performed. In some embodiments, the numerical simulations include Monte Carlo simulations of light propagation in tissue, which determines energy density due to photon absorption. In some embodiments, the numerical simulations also include thermal modeling of heat produced by laser sources interacting with photon-absorption heat. In some embodiments, the numerical simulations were performed for an external cuff (e.g., see cuff 1401 of FIG. 14A) placed around the femoral nerve in the leg. In some embodiments, the simulations were based on a structure similar to a FINE (flat interface nerve electrode) device such as described by U.S. patent application Ser. No. 13/117,122 (which issued as U.S. Pat. No. 8,652,187 on Feb. 18, 2014), titled "CUFF APPARATUS AND METHOD FOR OPTICAL AND/OR ELECTRICAL NERVE STIMULATION OF PERIPHERAL NERVES, which is incorporated herein by reference in its entirety, except that the electrodes of the FINE device were replaced with optically emitting vertical-cavity-surface-emitting lasers (VCSELs) for the thermal simulations of the present FINOS (flat interface nerve optical stimulator) and/or FINEOS (flat interface nerve electrode-optical stimulator) device 1401. An electrode-optical stimulator is also called an optrode. In some embodiments, configuring device 1401 as an external cuff (i.e., a cuff that is implanted within the body of the patient, but which is outside of the nerve bundle) with the optical devices replacing the electrodes of a conventional FINE device avoids penetrating the nerve and also provides greater access to fascicles (bundles of neurons comprising a nerve) (for example, a FINOS/FINEOS device is placed around the nerve bundle and squishes the nerve bundle in order to separate and expose the various nerves within the nerve bundle for independent stimulation).

In some embodiments, numerical simulations were performed for a penetrating array 1502 (see FIG. 15A) placed in the median or ulnar nerve in the arm.

FIG. 8A is a table 801 of pulse-signal characteristics associated with a computer simulation of a plurality of aperture sizes for an infrared-light nerve stimulation device. In some embodiments, the pulse-signal characteristics are calculated based on an energy-density requirement having a value of about 0.4 joules-per-square-centimeter (0.4 J/cm$^2$) (i.e., in some embodiments, the energy density required for stimulation at the surface of the tissue to be stimulated is 0.4 J/cm$^2$). In some embodiments, the available power density of VCSELs used in the infrared-light nerve stimulation device has a value of about 160 W/cm$^2$ (e.g., in some embodiments, 159154.9 milliwatts-per-square-centimeter (159.1549 W/cm$^2$).

FIG. 8B is a graph 802 of the simulated penetration depth versus pulse-energy-per-penetration-depth according to the data in table 801. Graph 802 shows the diminishing returns of penetration depth with respect to pulse energy.

FIG. 8C is a graph 803 showing isotemperature contour lines of the simulated temperature profiles resulting from different aperture diameters versus penetration depth according to the data in table 801. Approximate temperature values for the five areas of the temperature profile are based on an arbitrary temperature scale of 4 (coolest) to 18 (hottest) and are shown on the 1100-μm aperture portion of FIG. 8C only for clarity.

FIG. 9A is a graph 901 showing isotemperature contour lines of simulated temperature profiles in a tissue resulting from a simulated exposure to a ten-second-duration pulse train (at a 15-Hz pulse-repetition rate) from an infrared-light nerve stimulation device having a 600-μm aperture. In some embodiments, the simulation is based on a value of required tissue-surface irradiance for nerve stimulation of about 0.4 J/cm$^2$. After 10 seconds, the tissue surface is 46 degree Celsius, which is high enough to cause cell death. The scale of the temperature profile is calculated by subtracting 310.15 from the value of the actual surface temperature of the tissue measured in Kelvins. For example, the maximum temperature of 46 degrees Celsius (319.15 Kelvin) at the surface of the tissue is shown as about a 9 on the temperature-profile scale that runs from 1 (coolest) to 9 (hottest).

FIG. 9B is a graph 902 showing the simulated temperature change (delta T in degrees Celsius) one millimeter under the tissue surface versus time (seconds).

FIG. 9C is a table 903 showing the pulse-signal characteristics associated with a computer simulation of the 600-μm aperture.

FIG. 9D is a table 904 showing the physical characteristics of the tissue being stimulated during the computer simulation of the 600-μm aperture.

FIG. 10A is a graph 1001 showing isotemperature contour lines of simulated temperature profiles in a tissue resulting from a simulated exposure to a ten-second-duration pulse train (at a 15-Hz pulse-repetition rate) from an infrared-light nerve stimulation device having a 400-μm aperture. In some embodiments, the simulation is performed assuming a surface irradiance having a value of about 0.52 J/cm$^2$ (above the required surface irradiance for nerve stimulation of 0.4 J/cm$^2$), and the scale of the temperature profile is degrees Celsius. After 10 seconds, the tissue surface is 42.5 degrees Celsius.

FIG. 10B is a graph 1002 showing the maximum temperature of the tissue surface (degrees Celsius) versus time (seconds).

FIG. 10C is a table 1003 showing the pulse-signal characteristics used in a computer simulation of stimulation light from a 400-μm aperture at a surface irradiance having a value of about 0.52 J/cm².

FIG. 10D is a table 1004 showing the physical characteristics of the tissue being simulated with light stimulation from a 400-μm aperture (and an irradiance of 0.52 J/cm²).

FIG. 11A is a graph 1101 showing isotemperature contour lines of simulated temperature profiles in a tissue resulting from a simulated exposure to a ten-second pulse train (at a 9-Hz pulse-repetition rate) from an infrared-light nerve stimulation device having a 400-μm aperture. In some embodiments, the simulation is performed at a surface irradiance having a value of about 0.8 J/cm², the temperature scale is in degrees Celsius, and the pulse repetition rate is decreased to nine Hertz (9 Hz) to keep the tissue temperature under 43 degrees Celsius. After 10 seconds, the tissue surface is 43 degree Celsius. The scale of the temperature profile is degrees Celsius.

FIG. 11B is a graph 1102 showing the maximum temperature of the tissue surface (in degrees Celsius) versus time (in seconds) for a pulse train of 2.5-millisecond pulses each having 1.04 mJ.

FIG. 11C is a table 1103 showing the pulse-signal characteristics used in a computer simulation of stimulation light from a 400-μm aperture at a surface irradiance having a value of about 0.8 J/cm².

FIG. 11D is a table 1104 showing the physical characteristics of the tissue being simulated with light stimulation from the 400-μm aperture (and an irradiance of 0.8 J/cm²).

FIG. 11E is a graph 1105 of temperature down the center of the aperture (degrees Celsius) versus depth (meters).

FIG. 12A is a graph 1201 showing isotemperature contour lines of simulated temperature profiles in a tissue resulting from a simulated exposure to a ten-second pulse train from an infrared-light nerve stimulation device having a 400-μm aperture and three channels having one-millimeter (1-mm) spacing between each channel. In some embodiments, the simulation is performed at a surface irradiance having a value of about 0.4 J/cm² and the temperature scale is in degrees Celsius. In some embodiments, when the 1-mm channel spacing is used, the tissue temperature does not exceed 43 degrees Celsius, which minimizes the risk of thermal tissue damage due to the direct laser pulse.

Figures 12B, 12C:
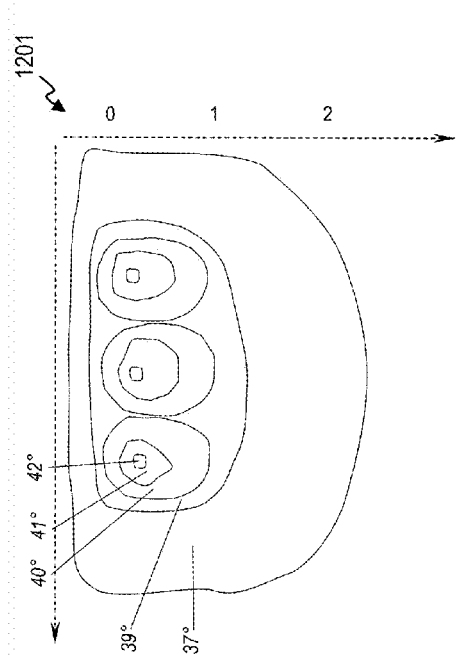
FIG. 12B is a table 1202 showing the pulse-signal characteristics used in a computer simulation of stimulation light from a 400-μm aperture having three channels at one-millimeter (1-mm) spacing.
FIG. 12C is a table 1203 showing the physical characteristics of the tissue being stimulated with light stimulation during the three-channel simulation.

FIG. 12B is a table 1202 showing the pulse-signal characteristics used in a computer simulation of stimulation light from a 400-μm aperture having three channels at one-millimeter (1-mm) spacing.

FIG. 12C is a table 1203 showing the physical characteristics of the tissue being simulated with light stimulation during the three-channel simulation.

FIG. 13A1 is another diagram of INS-plus-therapeutic-heat device 702 of FIG. 7B.

FIG. 13A2 is a simulated temperature profile 1301 for an external-cuff-stimulation device such as INS-plus-therapeutic-heat device 702 of FIG. 7B. In some embodiments, most of the light is absorbed in the first 200 μm of tissue, and this drives the required aperture to greater than 400 μm and subsequently the total heat dissipated in the implant is quite large. In some such embodiments, the heat load is the limiting factor for channel scaling.

FIG. 13A3 is detailed schematic diagram of INS-plus-therapeutic-heat unit 703A used for some embodiments of upper cuff portion 703 of FIG. 7B and FIG. 13A1. In some embodiments, unit 703A includes a plurality of vertical-cavity-surface-emitting lasers (VCSELs) 705, wherein each VCSEL 705 is operatively coupled to its own heat spreader 710, and wherein the plurality of VCSELs 705 and the plurality of heat spreaders 710 are contained within a silicone body 706. In some such embodiments, each of the VCSELs 705 emit a plurality of optical-stimulation signals 1305 and each of the heat spreaders 710 transfer heat 1310 generated by its respective VCSEL 705 away from that respective VCSEL 705.

FIG. 13A4 is detailed schematic diagram of INS-plus-therapeutic-heat unit 703B used for some embodiments of upper cuff portion 703 of FIG. 7B and FIG. 13A1. In some embodiments, unit 703B includes a plurality of VCSELs contained in a single package 1325 (e.g., in some embodiments, a VCSEL array), wherein a plurality of heat spreaders 710 are operatively coupled to the package of VCSELs 1325, and wherein the package of VCSELs 1325 and the plurality of heat spreaders 710 are contained within a silicone body 706. In some such embodiments, the package of VCSELs 1325 emit a plurality optical-stimulation signals 1305 and each of the heat spreaders 710 transfer heat 1310 away from the package of VCSELs 1325.

FIG. 13B is a table 1302 showing the pulse-signal characteristics associated with a computer simulation of the temperature profile 1301.

FIG. 13C is a table 1303 showing the physical characteristics of the tissue being stimulated during the computer simulation of the temperature profile 1301.

Figure 14B:
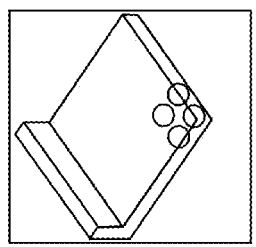
FIG. 14B is a perspective view of one-eighth of a 3-way-symmetrical model 1402 of device 1401 that was simulated to solve using symmetry.
Figure 14D:
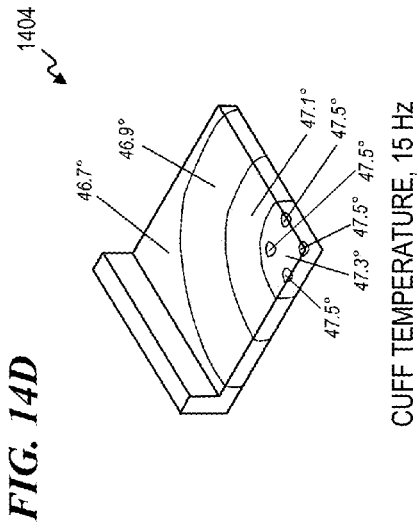
FIG. 14D is a graph 1404 showing isotemperature contour lines of simulated temperature profiles in the model 1402 of FIG. 1401, with a pulse repetition rate of 15 pulses per second.
Figure 14A:
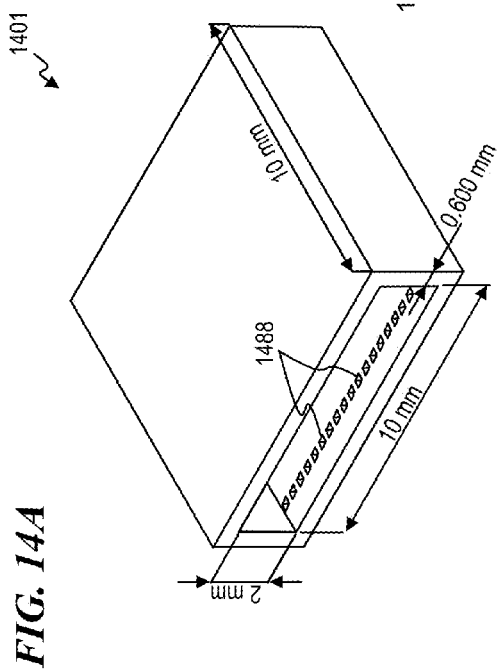
FIG. 14A is a perspective view of an external-cuff-stimulation device 1401.

FIG. 14A is a perspective view of an external-cuff-stimulation device 1401. In some embodiments, device 1401 includes 18 vertical-cavity-surface-emitting lasers (VCSELs) 1488 (e.g., shown here in FIG. 14A as a one-by-eighteen array; however, the thermal simulation of FIG. 14B used a three-by-three (3×3) array, on each of two sides), a 400-μm aperture, 2.5-milliseconds duration, X-pitch of one millimeter (1 mm), Z-pitch of 1 mm, and a 200-milliwatt (200-mW) peak-power output. In some embodiments, device 1401 is made from a material that includes silicon. In some embodiments, the dimensions of device 1401 are ten millimeters (10 mm) in length by two millimeters (2 mm) in height by ten millimeters (10 mm) in width (along the nerve). In some embodiments, the VCSEL efficiency is approximately 25%.

FIG. 14B is a perspective view of one-eighth of a 3-way-symmetrical model 1402 of device 1401 that was simulated to solve using symmetry. In some embodiments, no perfusion was taken into account for the simulation analysis.

Figure 14C:
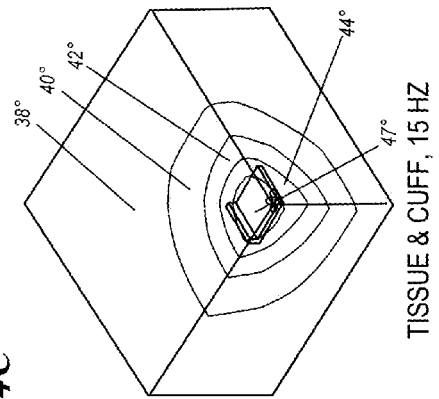
FIG. 14C is a graph 1403 showing isotemperature contour lines of simulated temperature profiles in both a tissue being simulated and the model 1402 of FIG. 1401, with a pulse repetition rate of 15 pulses-per-second.

FIG. 14C is a simulated temperature profile 1403 of both the tissue being simulated and the model 1402. In some embodiments, the simulation analysis shows an approximately 10° C. temperature rise while turning on all VCSELs at a fifteen-Hertz (15-Hz) pulse-repetition rate. Temperature profile 1403 represents a model of some embodiments of the present invention. However, other embodiments may exhibit different thermal characteristics.

FIG. 14D is a simulated temperature profile 1404 of model 1402 itself. In some embodiments, the temperature gradient across model 1402 is about 0.9° C., which is relatively small compared to the overall temperature rise. In some embodiments, the key factor is total heat load. In some embodiments, a 6 Hz repeat rate will result in 4° C. temperature rise and is more practical if no extra heat spreading is considered. Temperature profile 1404 represents a model of some embodiments of the present invention. However, other embodiments may exhibit different thermal characteristics.

Figures 15A, 15B:
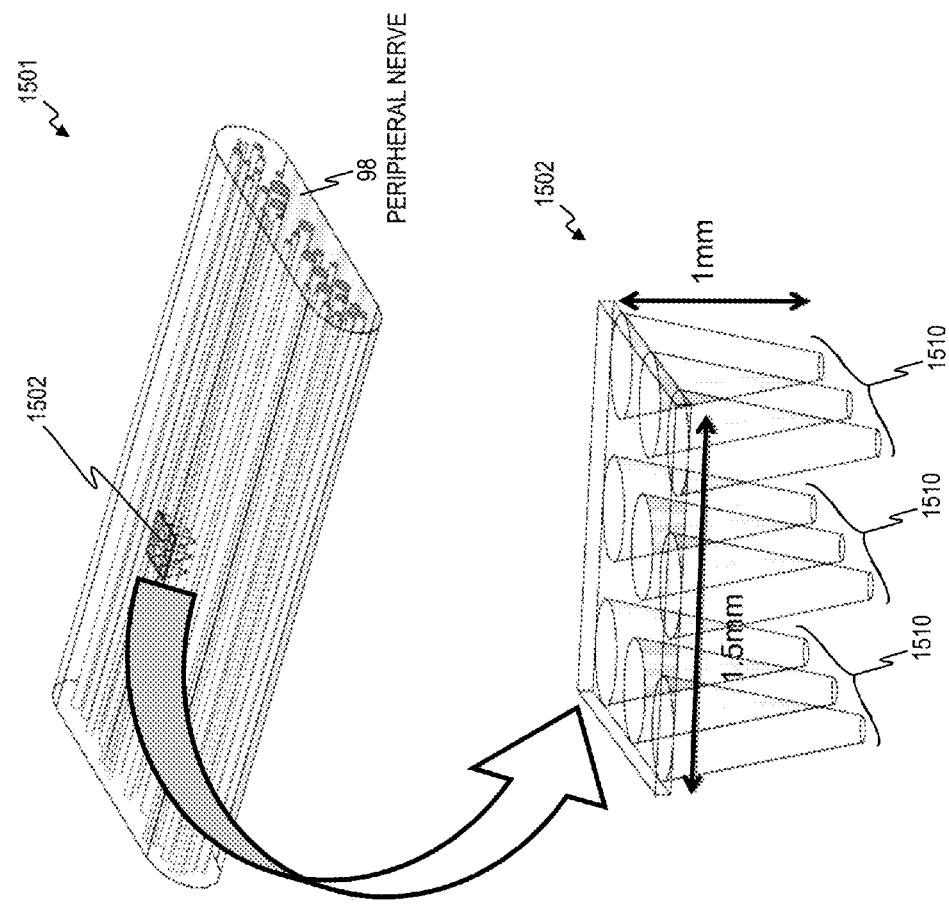
FIG. 15A is a perspective view of a penetrating array nerve stimulation system 1501.
FIG. 15B is a perspective view of spike electrodes/optrodes device 1502.

FIG. 15A is a perspective view of a penetrating array nerve stimulation system 1501. In some such embodiments, in order to obtain better access to all fascicles of peripheral nerve 98, the outer epineurium of nerve 98 is penetrated with a "spike" electrodes/optrodes device 1502.

FIG. 15B is a perspective view of spike electrodes/optrodes device 1502. In some embodiments, VCSELs are placed at the base of each cone 1510 of device 1502, which is inserted into nerve 98 of FIG. 15A. In some embodiments, the VCSELs are in a 3×3 array with a 500 µm pitch (in some such embodiments, an individual 3×3 array has a width of approximately 1.5 millimeters (mm)) In some embodiments, Zemax® optical-modeling using software from Zemax (Radiant ZEMAX, LLC, 3001 112th Avenue NE, Suite 202, Bellevue, Wash. 98004 USA; www.zemax.com) is performed to determine the light output of the cones 1510. In some embodiments, the overall heat load is determined for repetition rates up to 15 Hertz (Hz).

FIG. 16A is a simulated temperature profile 1601 conducted for a penetrating array nerve stimulation system 1602. In some embodiments, system 1601 is inserted into a peripheral nerve 98. In some embodiments, using system 1602 to penetrate into nerve 98 exacerbates the optical penetration depth limitation suffered by an external array system. In some such embodiments, the smaller aperture size facilitates larger energy density in the tissue, which allows the threshold to be reached with less wasted heat dissipation into the tissue.

FIG. 16B is a magnified view of simulated temperature profile 1601 showing the simulated temperature profile near system 1602. In some embodiments, system 1602 includes a heat spreader 1620 (in some embodiments, heat spreader 1620 has dimensions of 3 mm×3 mm×0.5 mm) configured to dissipate heat generated by spike electrodes/optrodes device 1630.

FIG. 16C is a table 1603 showing the pulse-signal characteristics associated with simulated computer simulation of temperature profile 1601.

FIG. 16D is a table 1604 showing the physical characteristics of the tissue being stimulated during the computer simulation of the temperature profile 1601.

FIG. 16E is a graph 1605 showing the maximum temperature down the center of the aperture (degrees Celsius) versus time (seconds).

In some embodiments, the present invention provides an apparatus that includes an infrared-light nerve stimulation-plus-therapeutic-heat (INS-plus-TH) device configured to be implanted in an animal, wherein the INS-plus-TH device includes: a plurality of lasers that output infrared laser-light nerve-stimulation signals and generate heat; a controller operatively coupled to control the plurality of lasers; and a plurality of thermally conductive material extensions that lead away from the INS-plus-TH device and spread the heat away from the lasers into surrounding tissue of the animal. In some embodiments, the INS-plus-TH device is configured to provide pain relief by stimulation of nerves of the body of the patient (e.g., peripheral nerves, dorsal roots, spinal cord, the brain, and any other suitable locations in the body of the animal). In some embodiments, therapeutic heat is provided by the apparatus to enhance the efficacy of the pain relief.

In some embodiments of the apparatus, the plurality of lasers is centrally located in the INS-plus-TH device and the thermally conductive material extensions protrude away from the lasers in a plurality of directions (e.g., a "Spider Cuff" design such as shown in FIG. 5). In some such embodiments, the thermally conductive material extensions include flexible copper wires. In some embodiments, the thermally conductive material extensions include carbon nanotubes (CNTs). In some embodiments, the thermally conductive material extensions include heat pipes.

In some embodiments of the apparatus, the plurality of thermally conductive material extensions is coated with a bio-compatible material. In some embodiments, the plurality of lasers includes a plurality of vertical-cavity-surface-emitting lasers (VCSELs). In some embodiments, the INS-plus-TH device is configured as a cuff electrode such that the plurality of VCSELs is located on a first side of a peripheral nerve and the plurality of thermally conductive material extensions are located on a second side of the peripheral nerve, opposite the first side.

In some embodiments, the present invention provides a method that includes providing an infrared-light nerve stimulation-plus-therapeutic-heat (INS-plus-TH) device that includes a plurality of lasers configured to emit infrared laser-light nerve-stimulation signals and a plurality of thermally conductive extensions configured to transfer heat generated by the plurality of lasers away from the plurality of lasers; implanting the INS-plus-TH device into an animal; emitting a plurality of infrared laser-light nerve-stimulation signals toward neural tissue of the animal from the plurality of lasers, wherein the emitted infrared laser-light nerve-stimulation signals are configured to generate action potentials in the neural tissue of the animal, and wherein the emitting of the plurality of infrared laser-light nerve-stimulation signals includes generating heat; and transferring the heat generated by the plurality of lasers during the emitting of the plurality of infrared laser-light nerve-stimulation signals away from the plurality of lasers and into surrounding tissue of the animal using the plurality of thermally conductive extensions. In some embodiments, the INS-plus-TH method provides pain relief by stimulating nerves of the body of the patient (e.g., peripheral nerves, dorsal roots, spinal cord, the brain, and any other suitable locations in the body of the animal). In some embodiments, the method further includes applying therapeutic heat to the tissue to enhance the efficacy of the pain relief.

In some embodiments of the method, the implanting of the INS-plus-TH device includes wrapping the INS-plus-TH device around a peripheral nerve of the animal such that the plurality of lasers is located on a first side of the peripheral nerve and the plurality of thermally conductive extensions are located on a second side of the peripheral nerve, opposite the first side.

In some embodiments of the method, the method further includes coating the plurality of thermally conductive extensions in a bio-compatible material. In some embodiments, the plurality of lasers is configured in a light-transmitting waveguide array, and the implanting includes implanting the waveguide array directly into the neural tissue of the animal.

In some embodiments of the method, the plurality of lasers are operatively coupled to a plurality of waveguides, and the emitting of the plurality of infrared laser-light nerve-stimulation signals includes reflecting the plurality of nerve-stimulation signals out of the plurality of waveguides in a substantially radial direction relative to the light-propagation axis of the plurality of waveguides. In some embodiments, the plurality of lasers are operatively coupled to a plurality of waveguides, and the emitting of the plurality of infrared laser-light nerve-stimulation signals includes diffusing the plurality of nerve-stimulation signals out of the plurality of waveguides in a substantially axial direction relative to the light-propagation axis of the plurality of waveguides. In some embodiments, the plurality of lasers are operatively coupled to a plurality of waveguides, and the emitting of the plurality of infrared laser-light nerve-stimulation signals includes collimating the plurality of nerve-stimulation signals out of the plurality of waveguides in a parallel beam in a substantially axial direction relative to the light-propagation axis of the plurality of waveguides.

In some embodiments, the present invention provides an apparatus that includes an infrared-light nerve stimulation-plus-therapeutic-heat (INS-plus-TH) device configured to be implanted in an animal, wherein the device includes: means for emitting a plurality of infrared laser-light nerve-stimulation signals toward neural tissue of the animal, wherein the emitted infrared laser-light nerve-stimulation signals are configured to generate action potentials in the neural tissue of the animal, and wherein the operation of the means for emitting generates heat; and means for transferring the heat generated during operation of the means for emitting the plurality of nerve-stimulation signals into surrounding tissue of the animal. In some embodiments, the INS-plus-TH apparatus provides pain relief by means for stimulating nerves of the body of the patient (e.g., peripheral nerves, dorsal roots, spinal cord, the brain, and any other suitable locations in the body of the animal). In some embodiments, the apparatus further includes means for applying therapeutic heat to the tissue to enhance the efficacy of the pain relief.

In some embodiments of the apparatus, the INS-plus-TH device is configured to be wrapped around a peripheral nerve of the animal such that the means for emitting the plurality of nerve-stimulation signals is located on a first side of the peripheral nerve and the means for transferring heat is located on a second side of the peripheral nerve, opposite the first side.

In some embodiments of the apparatus, the means for emitting the plurality of nerve-stimulation signals includes a plurality of waveguides, and the means for emitting further includes means for reflecting the plurality of nerve-stimulation signals out of the plurality of waveguides in a substantially radial direction relative to the light-propagation axis of the plurality of waveguides. In some embodiments, the means for emitting the plurality of nerve-stimulation signals includes a plurality of waveguides, and the means for emitting further includes means for diffusing the plurality of nerve-stimulation signals out of the plurality of waveguides in a substantially axial direction relative to the light-propagation axis of the plurality of waveguides. In some embodiments, the means for emitting the plurality of nerve-stimulation signals includes a plurality of waveguides, and the means for emitting further includes means for collimating the plurality of nerve-stimulation signals out of the plurality of waveguides in a parallel beam in a substantially axial direction relative to the light-propagation axis of the plurality of waveguides. In some embodiments, the means for emitting includes a plurality of vertical-cavity-surface-emitting lasers (VCSELs).

In some embodiments, the present invention provides an apparatus that includes an infrared-light nerve stimulation-plus-therapeutic-heat (INS-plus-TH) device configured to be implanted in an animal, wherein the INS-plus-TH device includes: a plurality of light sources that output infrared-light signals that are efficacious for nerve stimulation, wherein the light sources generate heat; a controller operatively coupled to control the plurality of light sources; and a plurality of thermally conductive material extensions that lead away from the INS-plus-TH device and spread the heat into surrounding tissue of the animal and away from at least one of the group consisting of the light sources and the controller.

In some embodiments of the apparatus, the plurality of light sources are centrally located in the INS-plus-TH device and the thermally conductive material extensions protrude away from the plurality of light sources in a plurality of directions. In some embodiments, the thermally conductive material extensions include copper wires. In some embodiments, the thermally conductive material extensions include carbon nanotubes (CNTs). In some embodiments, the plurality of light sources includes a plurality of lasers.

In some embodiments of the apparatus, the plurality of light sources includes a first array having a plurality of vertical-cavity-surface-emitting lasers (VCSELs). In some such embodiments, the INS-plus-TH device is configured as a cuff stimulator having the first array of VCSELs located on a first side of a peripheral nerve and a second array having a plurality of VCSELs located on a second side of the peripheral nerve, opposite the first side, with the plurality of thermally conductive material extensions extending in a direction parallel to a longitudinal axis of the peripheral nerve.

In some embodiments, the present invention provides a method for providing infrared-light nerve stimulation-plus-therapeutic-heat (INS-plus-TH), the method including providing a plurality of light sources configured to emit infrared-light nerve-stimulation signals; providing a plurality of thermally conductive extensions configured to transfer heat generated by the plurality of light sources away from the plurality of light sources; implanting the plurality of light sources and the plurality of thermally conductive extensions into an animal; emitting a plurality of infrared-light nerve-stimulation signals toward neural tissue of the animal from the plurality of light sources, wherein the emitted infrared-light nerve-stimulation signals are configured to generate action potentials in the neural tissue of the animal, and wherein the emitting of the plurality of infrared-light nerve-stimulation signals includes generating heat; controlling the emitting of the plurality of infrared-light nerve-stimulation signals to generate action potentials in the neural tissue; and transferring the heat generated by the plurality of light sources during the emitting of the plurality of infrared-light nerve-stimulation signals away from the plurality of light sources and into surrounding tissue of the animal using the plurality of thermally conductive extensions.

In some embodiments of the method, the implanting further includes locating a first subset of the plurality of light sources on a first side of a peripheral nerve of the animal; locating a second subset of the plurality of light sources on a second side of the peripheral nerve of the animal, opposite the first side; and locating the plurality of thermally conductive extensions such that the plurality of thermally conductive extensions extend in a direction parallel to a longitudinal axis of the peripheral nerve.

In some embodiments of the method, the plurality of light sources includes a plurality of lasers. In some embodiments, the plurality of lasers is configured in a light-transmitting waveguide array, wherein the implanting includes implanting the waveguide array directly into the neural tissue of the animal.

In some embodiments of the method, the providing of the plurality of light sources includes providing a plurality of waveguides operatively coupled to the plurality of light sources, and wherein the emitting of the plurality of infrared-light nerve-stimulation signals includes reflecting the plurality of nerve-stimulation signals out of the plurality of waveguides in one or more substantially radial directions relative to a light-propagation axis of the plurality of waveguides. In some embodiments, the providing of the plurality of light sources includes providing a plurality of waveguides operatively coupled to the plurality of light sources, and wherein the emitting of the plurality of infrared light source-light nerve-stimulation signals includes diffusing the plurality of nerve-stimulation signals out of the plurality of waveguides in a substantially axial direction relative to a light-propagation axis of the plurality of waveguides. In some embodiments, the providing of the plurality of light sources includes providing a plurality of waveguides and providing an array of vertical-cavity-surface-emitting lasers (VCSELs) operatively coupled to the plurality of waveguides, and wherein the emitting of the plurality of infrared-light nerve-stimulation signals includes collimating the plurality of nerve-stimulation signals out of the plurality of waveguides in parallel beams in a substantially axial direction relative to a light-propagation axis of the plurality of waveguides.

In some embodiments, the present invention provides an apparatus that includes an infrared-light nerve stimulation-plus-therapeutic-heat (INS-plus-TH) device configured to be implanted in an animal, wherein the device includes: means for emitting a plurality of infrared-light nerve-stimulation signals toward neural tissue of the animal, wherein the emitted infrared-light nerve-stimulation signals are configured to generate action potentials in the neural tissue of the animal, and wherein the means for emitting generate heat; means for controlling the means for emitting; and means for transferring the heat generated by the means for emitting away from the means for emitting and into surrounding tissue of the animal.

In some embodiments of the apparatus, the means for emitting includes a plurality of lasers. In some embodiments, the apparatus further includes array means for directly implanting the means for emitting into the neural tissue of the animal. In some embodiments, the means for emitting includes a plurality of waveguides, and wherein the means for emitting further includes means for reflecting the plurality of nerve-stimulation signals out of the plurality of waveguides in one or more substantially radial directions relative to a light-propagation axis of the plurality of waveguides. In some embodiments, the means for emitting includes a plurality of waveguides, and wherein the means for emitting further includes means for diffusing the plurality of nerve-stimulation signals out of the plurality of waveguides in a substantially axial direction relative to a light-propagation axis of the plurality of waveguides. In some embodiments, the means for emitting includes a plurality of waveguides and a plurality of vertical-cavity-surface-emitting lasers (VCSELs) operatively coupled to the plurality of waveguides, and wherein the means for emitting further includes means for collimating the plurality of nerve-stimulation signals out of the plurality of waveguides in parallel beams in a substantially axial direction relative to a light-propagation axis of the plurality of waveguides.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment). Further, some embodiments include fewer than all the components described as part of any one of the embodiments described herein.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:
    an infrared-light nerve stimulation-plus-therapeutic-heat (INS-plus-TH) device configured to be implanted in an animal, wherein the INS-plus-TH device includes:
        a plurality of light sources that output infrared-light signals that are efficacious for nerve stimulation, wherein the light sources generate heat, wherein the plurality of light sources includes a first array having a first plurality of vertical-cavity-surface-emitting lasers (VCSELs);
        a controller operatively coupled to control the plurality of light sources; and
        a plurality of thermally conductive material extensions that lead away from the INS-plus-TH device and spread the heat into surrounding tissue of the animal and away from at least one of the group consisting of the light sources and the controller
    wherein the INS-plus-TH device is configured as a cuff stimulator having the first array of VCSELs located on a first side of a peripheral nerve and a second array having a second plurality of VCSELs located on a second side of the peripheral nerve, opposite the first side, with the plurality of thermally conductive material extensions extending in a direction parallel to a longitudinal axis of the peripheral nerve.

2. The apparatus of claim 1, wherein the plurality of light sources are centrally located in the INS-plus-TH device and the thermally conductive material extensions protrude away from the plurality of light sources in a plurality of directions.

3. The apparatus of claim 1, wherein the thermally conductive material extensions include copper wires.

4. The apparatus of claim 1, wherein the thermally conductive material extensions include carbon nanotubes (CNTs).

5. The apparatus of claim 1, wherein each VCSEL of the first plurality of VCSELs is operatively coupled to its own thermally conductive material extension of the plurality of thermally conductive material extensions.

6. The apparatus of claim 1, wherein the first plurality of VCSELs is contained in a single package, and wherein a first subset plurality of the plurality of thermally conductive material extensions is operatively coupled to the single package of VCSELS.

7. The apparatus of claim 1, wherein the first plurality of VCSELs is contained in a single package, wherein a first subset plurality of the plurality of thermally conductive material extensions is operatively coupled to the single package of VCSELS, and wherein the single package of VCSELS and the first subset plurality of thermally conductive material extensions are contained within a silicone body.

8. The apparatus of claim 1, further comprising a plurality of optical waveguides operatively coupled to the first plurality of VCSELs, and wherein the plurality of waveguides are configured to reflect the infrared-light signals out of the plurality of waveguides in one or more substantially radial directions relative to a light-propagation axis of the plurality of waveguides.

9. A method for providing infrared-light nerve stimulation-plus-therapeutic-heat (INS-plus-TH), the method comprising:

providing a plurality of light sources configured to emit infrared-light nerve-stimulation signals;

providing a plurality of thermally conductive extensions configured to transfer heat generated by the plurality of light sources away from the plurality of light sources;

implanting the plurality of light sources and the plurality of thermally conductive extensions into an animal; wherein the implanting further includes:

locating a first subset of the plurality of light sources on a first side of a peripheral nerve of the animal, locating a second subset of the plurality of light sources on a second side of the peripheral nerve of the animal, opposite the first side, and locating the plurality of thermally conductive extensions such that the plurality of thermally conductive extensions extend in a direction parallel to a longitudinal axis of the peripheral nerve;

emitting a plurality of infrared-light nerve-stimulation signals toward neural tissue of the animal from the plurality of light sources, wherein the emitted infrared-light nerve-stimulation signals are configured to generate action potentials in the neural tissue of the animal, and wherein the emitting of the plurality of infrared-light nerve-stimulation signals includes generating heat;

controlling the emitting of the plurality of infrared-light nerve-stimulation signals to generate action potentials in the neural tissue; and transferring the heat generated by the plurality of light sources during the emitting of the plurality of infrared-light nerve-stimulation signals away from the plurality of light sources and into surrounding tissue of the animal using the plurality of thermally conductive extensions.

10. The method of claim 9, wherein the plurality of light sources includes a plurality of lasers.

11. The method of claim 10, wherein the plurality of lasers is configured in a light-transmitting waveguide array, wherein the implanting includes implanting the waveguide array directly into the neural tissue of the animal.

12. The method of claim 9, wherein the providing of the plurality of light sources includes providing a plurality of waveguides operatively coupled to the plurality of light sources, and wherein the emitting of the plurality of infrared-light nerve-stimulation signals includes reflecting the plurality of nerve-stimulation signals out of the plurality of waveguides in one or more substantially radial directions relative to a light-propagation axis of the plurality of waveguides.

13. The method of claim 9, wherein the providing of the plurality of light sources includes providing a plurality of waveguides operatively coupled to the plurality of light sources, and wherein the emitting of the plurality of infrared light source-light nerve-stimulation signals includes diffusing the plurality of nerve-stimulation signals out of the plurality of waveguides in a substantially axial direction relative to a light-propagation axis of the plurality of waveguides.

14. The method of claim 9, wherein the providing of the plurality of light sources includes providing a plurality of waveguides and providing an array of vertical-cavity-surface-emitting lasers (VCSELs) operatively coupled to the plurality of waveguides, and wherein the emitting of the plurality of infrared-light nerve-stimulation signals includes collimating the plurality of nerve-stimulation signals out of the plurality of waveguides in parallel beams in a substantially axial direction relative to a light-propagation axis of the plurality of waveguides.

15. An apparatus comprising:

an infrared-light nerve stimulation-plus-therapeutic-heat (INS-plus-TH) device configured to be implanted in an animal, wherein the device includes:

means for emitting a plurality of infrared-light nerve-stimulation signals toward neural tissue of the animal, wherein the emitted infrared-light nerve-stimulation signals are configured to generate action potentials in the neural tissue of the animal, wherein the means for emitting generates heat, wherein a first subset of the means for emitting is located on a first side of a peripheral nerve of the animal, and wherein a second subset of the means for emitting is located at a second side of the peripheral nerve of the animal, opposite the first side;

means for controlling the means for emitting; and means for transferring the heat generated by the means for emitting away from the means for emitting and into surrounding tissue of the animal, wherein the means for transferring heat extend along a direction parallel to a longitudinal axis of the peripheral nerve.

16. The apparatus of claim 15, wherein the means for emitting includes a plurality of lasers.

17. The apparatus of claim 15, further comprising array means for directly implanting the means for emitting into the neural tissue of the animal.

18. The apparatus of claim 15, wherein the means for emitting includes a plurality of waveguides, and wherein the means for emitting further includes means for reflecting the plurality of nerve-stimulation signals out of the plurality of waveguides in one or more substantially radial directions relative to a light-propagation axis of the plurality of waveguides.

19. The apparatus of claim 15, wherein the means for emitting includes a plurality of waveguides, and wherein the means for emitting further includes means for diffusing the plurality of nerve-stimulation signals out of the plurality of waveguides in a substantially axial direction relative to a light-propagation axis of the plurality of waveguides.

20. The apparatus of claim 15, wherein the means for emitting includes a plurality of waveguides and a plurality of vertical-cavity-surface-emitting lasers (VCSELs) operatively coupled to the plurality of waveguides, and wherein the means for emitting further includes means for collimating the plurality of nerve-stimulation signals out of the plurality of waveguides in parallel beams in a substantially axial direction relative to a light-propagation axis of the plurality of waveguides.

* * * * *